United States Patent
Keitel

(10) Patent No.: US 12,251,540 B2
(45) Date of Patent: Mar. 18, 2025

(54) INJECTION DEVICE WITH FLEXIBLE DOSE SELECTION

(71) Applicant: MEDMIX SWITZERLAND AG, Haag (CH)

(72) Inventor: Joachim Keitel, Esslingen (DE)

(73) Assignee: Medmix Switzerland AG, Haag (CH)

( * ) Notice: Subject to any disclaimer, the term of this patent is extended or adjusted under 35 U.S.C. 154(b) by 0 days.

(21) Appl. No.: 18/205,966

(22) Filed: Jun. 5, 2023

(65) Prior Publication Data

US 2023/0302228 A1 Sep. 28, 2023

Related U.S. Application Data

(63) Continuation of application No. 16/888,086, filed on May 29, 2020, now Pat. No. 11,969,584, which is a
(Continued)

(51) Int. Cl.
| | |
|---|---|
| *A61M 5/315* | (2006.01) |
| *A61M 5/24* | (2006.01) |
| *A61M 5/50* | (2006.01) |

(52) U.S. Cl.
CPC .......... *A61M 5/3156* (2013.01); *A61M 5/24* (2013.01); *A61M 5/31536* (2013.01);
(Continued)

(58) Field of Classification Search
CPC .. A61M 5/3156; A61M 5/24; A61M 5/31536; A61M 5/3141; A61M 5/31551;
(Continued)

(56) References Cited

U.S. PATENT DOCUMENTS

| | | |
|---|---|---|
| 4,973,318 A | 11/1990 | Holm et al. |
| 5,279,586 A | 1/1994 | Balkwill |
| (Continued) | | |

FOREIGN PATENT DOCUMENTS

| | | |
|---|---|---|
| CN | 1784246 A | 6/2006 |
| CN | 101060874 A | 10/2007 |
| (Continued) | | |

OTHER PUBLICATIONS

Chinese Office Action issued Jan. 8, 2024 in corresponding Chinese Application 202210184867.1 (Google machine translation).
(Continued)

*Primary Examiner* — Tasnim Mehjabin Ahmed
(74) *Attorney, Agent, or Firm* — Global IP Counselors, LLP

(57) ABSTRACT

An injection device incorporating a dose setting mechanism is presented where the dose setting mechanism contains a dose selector having one or more dose stops corresponding to a finite set of predetermined fixed doses, where the set of finite predetermined fixed doses includes a lowest fixed dose and one or more higher fixed doses, and where at least one of the one or more higher fixed doses is equal to the lowest fixed dose plus a fractional amount of the lowest fixed dose. The dose setting mechanism can further include a floating spline that is rotationally engaged with a snap element such that the snap element can rotate relative to the floating spline during both dose setting and dose delivery.

19 Claims, 13 Drawing Sheets

Related U.S. Application Data continuation of application No. 15/649,287, filed on Jul. 13, 2017, now Pat. No. 10,688,247.

(52) U.S. Cl.
CPC .... *A61M 5/31541* (2013.01); *A61M 5/31551* (2013.01); *A61M 5/31553* (2013.01); *A61M 5/31563* (2013.01); *A61M 5/3157* (2013.01); *A61M 5/3158* (2013.01); *A61M 5/31593* (2013.01); *A61M 2005/3154* (2013.01); *A61M 5/50* (2013.01); *A61M 2205/581* (2013.01); *A61M 2205/582* (2013.01); *A61M 2207/00* (2013.01)

(58) Field of Classification Search
CPC .......... A61M 5/31553; A61M 5/31563; A61M 5/3157; A61M 5/3158; A61M 5/31593; A61M 5/50; A61M 2005/3154
See application file for complete search history.

(56) References Cited

U.S. PATENT DOCUMENTS

| | | | |
|---|---|---|---|
| 5,938,642 | A | 8/1999 | Burroughs et al. |
| 6,193,698 | B1 | 2/2001 | Kirchhofer et al. |
| 6,277,099 | B1 | 8/2001 | Strowe et al. |
| 6,582,404 | B1 | 6/2003 | Klitgaard et al. |
| 7,762,994 | B2 | 7/2010 | Klint et al. |
| 7,976,509 | B2 | 7/2011 | Moser et al. |
| 8,579,869 | B2 | 11/2013 | Klint et al. |
| 8,747,367 | B2 | 6/2014 | Keitel et al. |
| 9,265,893 | B2 | 2/2016 | Hansen et al. |
| 9,694,136 | B2 | 7/2017 | Keitel et al. |
| 10,004,852 | B2 | 6/2018 | Marsh et al. |
| 10,688,247 | B2 | 6/2020 | Keitel |
| 2002/0151855 | A1 | 10/2002 | Douglas et al. |
| 2004/0199117 | A1 | 10/2004 | Giambattista et al. |
| 2005/0165349 | A1 | 7/2005 | Stamp |
| 2005/0177115 | A1 | 8/2005 | Broennimann et al. |
| 2006/0206057 | A1 | 9/2006 | Deruntz et al. |
| 2007/0106227 | A1 | 5/2007 | Burren et al. |
| 2008/0147005 | A1 | 6/2008 | Moller et al. |
| 2008/0183139 | A1 | 7/2008 | Burren et al. |
| 2010/0114025 | A1 | 5/2010 | Møller |
| 2011/0034878 | A1 | 2/2011 | Radmer et al. |
| 2011/0034881 | A1 | 2/2011 | Bartha |
| 2011/0098658 | A1 | 4/2011 | Enggaard et al. |
| 2011/0270214 | A1 | 11/2011 | Jorgensen et al. |
| 2011/0313365 | A1 | 12/2011 | Wieselblad |
| 2012/0009181 | A1 | 1/2012 | Ab et al. |
| 2012/0095411 | A1 | 4/2012 | Harms et al. |
| 2012/0107783 | A1 | 5/2012 | Julian et al. |
| 2012/0157931 | A1 | 6/2012 | Nzike |
| 2012/0277683 | A1* | 11/2012 | Moller .............. A61M 5/31585 604/211 |
| 2012/0283647 | A1 | 11/2012 | Cronenberg et al. |
| 2012/0283659 | A1 | 11/2012 | Kouyoumjian et al. |
| 2012/0289907 | A1 | 11/2012 | Veasey et al. |
| 2012/0310206 | A1 | 12/2012 | Kouyoumjian et al. |
| 2013/0012885 | A1 | 1/2013 | Bode et al. |
| 2013/0197479 | A1 | 8/2013 | Butler et al. |
| 2014/0025016 | A1 | 1/2014 | Plumptre |
| 2014/0128808 | A1 | 5/2014 | Keitel |
| 2014/0249482 | A1 | 9/2014 | Wieselblad |
| 2014/0350480 | A1 | 11/2014 | Keitel |
| 2015/0080812 | A1 | 3/2015 | Enggaard et al. |
| 2015/0148750 | A1 | 5/2015 | Pedersen et al. |
| 2015/0157803 | A1 | 6/2015 | Radmer et al. |
| 2015/0202369 | A1 | 7/2015 | Melander et al. |
| 2015/0209518 | A1 | 7/2015 | Moser et al. |
| 2015/0374924 | A1 | 12/2015 | Keitel et al. |
| 2016/0008549 | A1 | 1/2016 | Plumptre et al. |
| 2016/0015904 | A1 | 1/2016 | Plumptre et al. |
| 2016/0045665 | A1 | 2/2016 | Bayer et al. |
| 2016/0051766 | A1 | 2/2016 | Marsh et al. |
| 2016/0051769 | A1 | 2/2016 | Jones et al. |
| 2016/0067414 | A1 | 3/2016 | Bayer et al. |
| 2016/0101234 | A1 | 4/2016 | Bock et al. |
| 2016/0129187 | A1 | 5/2016 | Roervig et al. |
| 2016/0129196 | A1 | 5/2016 | Hirschel et al. |
| 2016/0136358 | A1 | 5/2016 | Oakley et al. |
| 2016/0151572 | A1 | 6/2016 | Oakley et al. |
| 2016/0151581 | A1 | 6/2016 | Giambattista et al. |
| 2016/0158454 | A1 | 6/2016 | Oakley et al. |
| 2016/0220759 | A1 | 8/2016 | Enggaard et al. |
| 2016/0228651 | A1 | 8/2016 | Plambech |
| 2016/0263320 | A1 | 9/2016 | Constantineau et al. |
| 2016/0263322 | A1 | 9/2016 | Cowe |
| 2016/0287812 | A1 | 10/2016 | Nielsen et al. |
| 2016/0296711 | A1 | 10/2016 | Blancke et al. |
| 2016/0317745 | A1 | 11/2016 | Neldsen et al. |
| 2016/0339181 | A1 | 11/2016 | Keitel |
| 2016/0346479 | A1 | 12/2016 | Keitel |
| 2016/0361499 | A1 | 12/2016 | Keitel |
| 2017/0043098 | A1 | 2/2017 | Kohlbrenner et al. |
| 2017/0304551 | A1 | 10/2017 | Eardley et al. |
| 2017/0319793 | A1 | 11/2017 | Bergens |
| 2018/0064880 | A1 | 3/2018 | Kiilerich |
| 2018/0071460 | A1 | 3/2018 | Rekaya et al. |
| 2018/0147364 | A1 | 5/2018 | Roervig et al. |
| 2018/0200446 | A1 | 7/2018 | Grimoldby et al. |
| 2018/0311442 | A1 | 11/2018 | Saussaye et al. |
| 2019/0015595 | A1 | 1/2019 | Keitel |
| 2019/0046734 | A1 | 2/2019 | Jakobsen et al. |
| 2019/0117898 | A1 | 4/2019 | Hirschel et al. |
| 2020/0023136 | A1 | 1/2020 | Keitel et al. |
| 2020/0164150 | A1 | 5/2020 | Smith et al. |
| 2020/0206428 | A1 | 7/2020 | Jakobsen et al. |
| 2020/0268977 | A1 | 8/2020 | Keitel et al. |
| 2020/0282147 | A1 | 9/2020 | Quinn et al. |
| 2020/0289762 | A1 | 9/2020 | Keitel |
| 2020/0376205 | A1 | 12/2020 | Keitel |
| 2020/0405958 | A1 | 12/2020 | Hacker et al. |
| 2021/0283340 | A1 | 9/2021 | Bengtsson et al. |
| 2022/0072233 | A1 | 3/2022 | Karlsson et al. |
| 2022/0118192 | A1 | 4/2022 | Keitel |

FOREIGN PATENT DOCUMENTS

| | | |
|---|---|---|
| CN | 1016411126 A | 2/2010 |
| CN | 101912649 A | 12/2010 |
| CN | 101939035 A | 1/2011 |
| CN | 102202711 A | 9/2011 |
| CN | 102448519 A | 5/2012 |
| CN | 102740910 A | 10/2012 |
| CN | 103153372 A | 6/2013 |
| CN | 104363939 A | 2/2015 |
| CN | 105025965 A | 11/2015 |
| CN | 105102036 A | 11/2015 |
| CN | 105246530 A | 1/2016 |
| CN | 105377333 A | 3/2016 |
| CN | 105377340 A | 3/2016 |
| CN | 105377342 A | 3/2016 |
| CN | 105377343 A | 3/2016 |
| CN | 105517605 A | 4/2016 |
| CN | 105611959 A | 5/2016 |
| CN | 105744975 A | 7/2016 |
| CN | 106132460 A | 11/2016 |
| CN | 206045102 U | 3/2017 |
| CN | 106794307 A | 5/2017 |
| CN | 107635605 A | 1/2018 |
| CN | 107995871 A | 5/2018 |
| CN | 108025137 A | 5/2018 |
| DE | 102006004561 A1 | 7/2007 |
| EP | 0730876 A2 | 3/1996 |
| EP | 0562029 B1 | 7/1999 |
| EP | 1074273 B1 | 2/2001 |
| EP | 1066847 B1 | 6/2004 |
| EP | 2283886 A2 | 2/2011 |
| EP | 2452711 A1 | 5/2012 |
| EP | 2812054 B1 | 6/2016 |
| EP | 3162397 A1 | 5/2017 |
| EP | 3181169 A1 | 6/2017 |

(56) References Cited

FOREIGN PATENT DOCUMENTS

| | | |
|---|---|---|
| EP | 3181170 A1 | 6/2017 |
| EP | 2244768 B1 | 4/2019 |
| ES | 2245945 T3 | 2/2006 |
| IN | 103547302 A | 1/2014 |
| JP | 2003510135 A | 3/2003 |
| JP | 2012507314 A | 3/2012 |
| JP | 2012521825 A | 9/2012 |
| JP | 2013506461 A | 2/2013 |
| JP | 2016507302 A | 3/2016 |
| JP | 2016514590 A | 5/2016 |
| JP | 2016515434 A | 5/2016 |
| JP | 2016518183 A | 6/2016 |
| JP | 2016518901 A | 6/2016 |
| JP | 2016524978 A | 8/2016 |
| TW | 201302260 A | 1/2013 |
| WO | 9210425 A1 | 6/1992 |
| WO | 0119434 A1 | 3/2001 |
| WO | 02053214 A1 | 7/2002 |
| WO | 2004078241 A1 | 9/2004 |
| WO | 2005072796 A2 | 8/2005 |
| WO | 2006045526 A1 | 5/2006 |
| WO | 2006045529 A1 | 5/2006 |
| WO | 2009014955 A2 | 1/2009 |
| WO | 2009092807 A1 | 7/2009 |
| WO | 2009114542 A1 | 9/2009 |
| WO | 2010052275 A2 | 5/2010 |
| WO | 2010081489 A1 | 7/2010 |
| WO | 2011068531 A1 | 6/2011 |
| WO | 2012105898 A1 | 8/2012 |
| WO | 2013117332 A1 | 8/2013 |
| WO | 2013155435 A1 | 10/2013 |
| WO | 2013178372 A1 | 12/2013 |
| WO | 2014005807 A1 | 1/2014 |
| WO | 2014161954 A1 | 10/2014 |
| WO | 2015036616 A1 | 3/2015 |
| WO | 2015090320 A2 | 6/2015 |
| WO | 2015145294 A1 | 10/2015 |
| WO | 2016001298 A1 | 1/2016 |
| WO | 2016083384 A1 | 6/2016 |
| WO | 2016142501 A1 | 9/2016 |
| WO | 2016198540 A2 | 12/2016 |
| WO | 2017001692 A1 | 1/2017 |
| WO | 2017081421 A1 | 5/2017 |
| WO | 2017102395 A1 | 6/2017 |
| WO | 2018046728 A1 | 3/2018 |
| WO | 2019011394 A1 | 1/2019 |
| WO | 2019197493 A1 | 10/2019 |
| WO | 2021214272 A1 | 10/2021 |

OTHER PUBLICATIONS

Chinese Office Action issued Jan. 8, 2024 in corresponding Chinese Application 202210184864.8 (Google machine translation).
Chinese Office Action issued Jan. 12, 2024 in corresponding Chinese Application 202210184868.6 (Google machine translation).
Extended European Search Report issued Jul. 6, 2022 in European Application No. 21168770.2.
Extended European Search Report issued Jul. 6, 2022 in European Application No. 21168836.1.
Extended European Search Report issued Jul. 6, 2022 in European Application No. 21168744.7.
Extended European Search Report issued Jul. 6, 2022 in European Application No. 21168911.2.
Extended European Search Report issued Jul. 6, 2022 in European Application No. 21168811.4.
Extended European Search Report issued Jul. 6, 2022 in European Application No. 21168901.3.
Notification of Reasons for Refusal issued Apr. 4, 2020 in Japanese Application No. 2022-068723.
Notification of Reasons for Refusal issued Apr. 4, 2020 in Japanese Application No. 2022-068724.
Notification of Reasons for Refusal issued Apr. 25, 2020 in Japanese Application No. 2022-068725.
Notification of Reasons for Refusal issued Apr. 25, 2020 in Japanese Application No. 2022-068727.
Examination Report issued Dec. 8, 2022 in Indian Application No. 202117037437.
Chinese Office Action issued Oct. 27, 2022 in Chinese Application No. 202080015161.1.
Japanese Office Action issued Mar. 28, 2023 in Japanese Application No. 2022-068728 (with Google translation).
European Search Report issued Nov. 22, 2022 in European Application No. 22192125.7.
European Search Report issued Nov. 23, 2022 in European Application No. 22192212.3.
European Search Report issued Oct. 25, 2023 in corresponding European Application 23176180.0.
European Search Report issued Oct. 6, 2023 in corresponding European Application 23168610.6.
Chinese Office Action issued Jan. 19, 2024 in corresponding Chinese Application 202210184869.0 (Google machine translation).
Chinese Office Action issued Jan. 8, 2024 in corresponding Chinese Application 202210704106.4 (Google machine translation).
European Search Report issued Sep. 12, 2023 in European Application No. 23168342.6.
Extended European Search Report issued Jul. 6, 2021 in European Application No. 21168770.2.
Extended European Search Report issued Jul. 6, 2021 in European Application No. 21168836.1.
Extended European Search Report issued Jul. 6, 2021 in European Application No. 21168744.7.
Extended European Search Report issued Jul. 5, 2021 in European Application No. 21168911.2.
Extended European Search Report issued Jul. 5, 2021 in European Application No. 21168811.4.
Extended European Search Report issued Jul. 6, 2021 in European Application No. 21168901.3.
Chinese Office Action issued Jun. 29, 2023 in Chinese Application No. 202080015161.1.
International Search Report and Written Opinion issued Jul. 26, 2023 in International Application No. PCT/EP2023/061187.
European Search Report issued Dec. 13, 2022 in European Application No. 22184328.7.
International Search Report and Written Opinion issued Jul. 26, 2023 in International Application No. PCT/EP2023/061175.
International Search Report and Written Opinion issued Jul. 26, 2023 in International Application No. PCT/EP2023/061173.
European Search Report issued Oct. 6, 2022 in European Application No. 22170342.4.
European Search Report issued Nov. 23, 2022 in European Application No. 22180552.6.
International Search Report and Written Opinion issued May 17, 2023 in International Application No. PCT/EP2023/061183.
European Search Report issued Dec. 2, 2022 in European Application No. 22183157.1.
International Search Report and Written Opinion issued Jul. 14, 2023 in International Application No. PCT/EP2023/061193.
International Search Report and Written Opinion issued May 23, 2023 in International Application No. PCT/EP2023/061184.
PCT Invitation to Pay Additional Fees (PCT/ISA/206) issued Mar. 14, 2018 in International Application No. PCT/EP2017/001140.
International Search Report and Written Opinion issued Jun. 14, 2018 in International Application No. EP2017/001140.
International Preliminary Report on Patentability issued Apr. 30, 2020 in International Application No. PCT/EP2019/067347.
Japanese Office Action issued Oct. 31, 2023 in corresponding Japanese Application 2021-547074.
Chinese Office Action issued Jan. 26, 2024 in corresponding Chinese Application 202210704107.9 (Google machine translation).
Chinese Office Action issued Jan. 19, 2024 in corresponding Chinese Application 202210184863.3 (Google machine translation).
Chinese Office Action issued Jan. 19, 2024 in corresponding Chinese Application 202210184866.7 (Google machine translation).
Non-Final Office Action issued Jul. 1, 2024 in corresponding U.S. Appl. No. 17/431,633.

(56) References Cited

OTHER PUBLICATIONS

Non-Final Office Action issued Jun. 21, 2024 in corresponding U.S. Appl. No. 18/205,957.
International Search Report and Written Opinion issued Mar. 20, 2024 in corresponding International Application PCT/EP2023/080161.
Second Examination Opinion Notice in the corresponding Chinese Patent Application No. 202210184868.6, dated Sep. 30, 2024 (Google Machine Translation).
European Patent Office communication corresponding to application No. 21168901.3-1122 dated Jan. 8, 2025 enclosing third party observations.

\* cited by examiner

INJECTION DEVICE WITH FLEXIBLE DOSE SELECTION

CROSS-REFERENCE TO RELATED APPLICATION

This application is a continuation application of U.S. application Ser. No. 16/888,086, filed May 29, 2020, which is a continuation application of U.S. application Ser. No. 15/649,287, filed on Jul. 13, 2017, the contents of each of which are incorporated herein by reference.

BACKGROUND

Technical Field

The present disclosure relates to an injection device and particularly to the dose setting mechanism of the injection device, where a user can select one or more predetermined fixed dose settings as a direct result of the design and manufacture of a single component of the dose setting mechanism. Changing the design of this single component of the dose setting mechanism allows for the efficient manufacture of injection devices that can be custom made for a specific dosing regimen and/or used in dose-ranging evaluations.

Background of the Invention

There are a number of medicament delivery devices on the market that are capable of automatically, semi-automatically or manually delivering doses of medicament. Of the known type of delivery devices the "pen-type" injector is gaining in popularity and is available in both reusable and disposable designs. Such devices are constructed with dose setting mechanisms that include a variety of inter-acting components for obtaining desired functions, such as setting a dose and then delivering the set dose. In most cases, these medicament delivery devices have only one or two single fixed dose setting or variable dose setting where each possible set dose must be a multiple of the lowest possible set dose. In other words, these existing variable dose injection devices do not allow a dose to be set that is a fraction of the lowest possible dose.

SUMMARY

The types of pen-type injector designs have a dose setting mechanism located at the distal end of the device and a medicament container, such as, a cartridge, located in the proximal end. The known injector designs typically are multiple (variable) dose devices, meaning that the user can select (dial) a dose between 0 and a maximum allowable settable dose. A dose dial sleeve is printed with a range of possible dose settings that typically correspond to each possible incremental dose setting. For example, if the injector is designed and manufactured with a maximum dose setting of 80 international units (IU), then each incremental settable dose differs by one IU. Stated differently, to set a dose of 60 IU, the user would rotate a dose setting knob through 60 possible dose settings while viewing the dose dial sleeve marking indicating each incremental dose until it showed 60 IU. Of course, there would be nothing to prevent a user from accidentally setting an under dose of 59 IU or an over dose of 61 HU, especially if the user is physically impaired, for example having reduced eyesight or severe arthritis.

As stated, some injection devices are manufactured and designed as so-called fixed dose designs where the dose dial sleeve contains printing signifying only one or two doses. The design idea behind these devices is for the user is to rotate the dose setting knob until one of the fixed dose settings is observed, typically in a window of the injector housing. However, in such injector designs the user is still required to step through individual equal incremental dose settings until the indicia of the fixed dose setting is observed in the window. Because the dose setting mechanism requires the user to physically step through each incremental dose setting there is nothing to prevent the user from stopping at a dose less than or greater than the fixed dose setting. In addition, the user will experience a haptic or audible notification as the dose setting mechanism is dialed through each incremental dose to arrive at the final dose setting.

Another drawback of the existing injector designs is the inability to have fixed doses that are not multiples of a single incremental value. In other words, if an injector is designed with a maximum settable dose of 80 IU, then typically each incremental dose would be 1 IU. As such, it would not be possible to set a dose of 2.3 IU. The user could only set a dose of 2 or 3 IU. Stated another way, fractional doses could not be set with such a dose setting mechanism. The ability to set fractional doses is important, especially during studies trying to determine optimum dose amounts for newly developed medicaments and/or for new patients using existing medicaments for the first time.

Although there exist many drug delivery devices available for patient use, there is clearly a need to have an injector available that can deliver one or more predetermined fixed doses where at least one of the predetermined fixed doses is a fractional amount of a second predetermined fixed dose. The availability of a pen-type injector where the user cannot set and/or deliver a dose that is not one of a number of predetermined fixed doses is also an important goal. And, it is highly desirable to have an injector design where only a single mechanical component of the dose setting mechanism needs to be redesigned and manufactured in order to change or vary the predetermined fix doses. This would allow cost effective manufacturing of injection devices that could be easily customized for patients to allow the injection of one or more effective doses of medicament specifically tailored to the particular user.

The disclosure presented below solves the above-mentioned problems with existing medicament delivery devices and provides an injector design that fulfills the needs and requirements mentioned above.

This disclosure presents a number of dose setting mechanism designs that allow an injection device to be set with one or more fractional predetermined fixed dose settings. The designs can also prevent the setting of an unintended dose, i.e., a dose other than one of the predetermined fixed dose settings. The dose setting designs provide a cost effective way of manufacturing an injection device because only a single component needs to be redesigned and manufactured in order to provide a complete injection device having one or more different predetermined fixed doses.

In one embodiment the dose setting mechanism includes a floating spline, a dose knob, a dose selector, and a snap element. The floating spline is rotationally engaged with the snap element, which has a fixed set of splines. The floating spline is engaged with a corresponding set of splines on the dose selector during dose setting and dose delivery. The floating spline comprises a plurality of longitudinally extending splines that are engaged with splines on the dose knob during dose delivery, but not so engaged during dose setting. The floating spline can also be axially fixed relative to the snap element.

The snap element rotates relative to the floating spline and the dose selector during both dose setting and dose delivery. This is due to the floating spline being rotationally fixed to the dose selector through corresponding splines on an inner surface of the dose selector. Since the dose selector is rotationally fixed to the housing through a splined connection, the engagement and meshing of the floating spline with the splines on the inner surface of the dose selector prevents rotation of the floating spine relative to the body during dose setting and dose delivery. The snap element is also configured with a flexible arm that has a radial extending protrusion that preferably projects outwardly in to engage a plurality of dose stops that are located on an inner surface of the dose selector. These dose stops are designed and manufactured, preferably through a molding process, to be spaced radially apart from each other such that they define a set of finite predetermined fixed doses. During the setting of one of the predetermined doses, the snap element is rotated relative to the dose selector to cause the protrusion on the snap element to engage with and travel over one of the dose stops. Once the protrusion travels over the dose stop and rotation is stopped, this position of the snap element defines a single fixed dose of medicament for delivery. The set of finite predetermined fixed doses includes a lowest fixed dose and one or more higher fixed doses.

The distance between the dose stops on the inner surface of the dose selector can be designed and manufactured such that the one or more higher fixed doses is not equal to an even multiple of the lowest fixed dose. This results in a fixed dose setting that includes a fractional amount of the lowest fixed dose. Stated differently, the distance between the dose stops can be manufactured, i.e., predetermined, such that at least one of the one or more higher fixed doses is equal to the lowest fixed dose plus a fractional amount of the lowest fixed dose. This is not possible with dose setting mechanisms currently known.

Because the finite predetermined fixed doses are defined only by the number of and relative spacing between dose stops, and those dose stops are uniquely located on a single component of the dose setting mechanism, i.e., the dose selector, this presents an efficient and cost effective method to change the set of finite predetermined fixed doses without manufacturing any other components of the dose setting mechanism. In other words, only the design of dose selector needs to be changed to result in the manufacture of a second dose selector, which can then replace the original dose selector during assembly of the injection device. No other components of the dose setting mechanism need replacement. In some cases, the printing that appears on a dose sleeve can be changed, but the design and manufacture of the dose sleeve remains the same. Replacement of the original dose selector with a second dose selector having a different arrangement of dose stops results in the dose setting mechanism having a different set of finite predetermined fixed doses.

The spatial relationship between the dose selector and the snap element changes between dose setting and dose delivery. There is a first fixed relative axial position between the snap element and the dose selector, which occurs during dose setting and there is a second fixed axial relative position that occurs during dose delivery. In the first fixed position, the protrusion can engage a dose stop. However, in the second fixed position the protrusion cannot engage a dose stop, wherein the first fixed relative position is achieved during dose setting and the second fixed relative position is achieved during dose delivery. At the completion of the dose delivery, the protrusion can engage with and travel over an end of injection bump to provide the user with a tactile and/or audible notification that the delivery is complete.

As mentioned, the dose setting mechanism of this disclosure can include a functional and structural feature that prevents a user from setting a dose other than one of the predetermined fixed doses, i.e., a so-called unintended dose. This fail-safe feature of the present disclosure prevents the setting of a dose other than one of the finite set of predetermined fixed doses by using a biasing member that exerts a counter rotation force on the snap element during the dose setting procedure. The biasing member can be a torsion spring operatively connected to the snap element through a connection with a dose sleeve. When a torsion spring is incorporated in the dose setting mechanism it is biased to a predetermined torque during assembly. The torque exerts a force on the snap element such that during dose setting by user dialing or rotating the dose knob, the snap element is urged to resist the rotational force applied by the user. Although this counter rotational torque is easily overcome by the user during the rotation of the dose knob, if the user were to release the dose knob for some reason the torque would cause the knob and the snap element to rotate in the opposite direction. In such an event, the torque is preferably sufficient to counter-rotate the snap element such that the protrusion will return to engage with a previous dose stop. In some instances, it can be desirable to use a biasing member that will counter rotate the snap element such that the protrusion will travel back to the zero dose hard stop. The fail-safe feature would only come into play if a user did not rotate the dose knob and snap element far enough so that the protrusion engages and travels over a next dose stop that corresponds to a higher fixed dose than the previous dose stop. As the dose knob is rotated during dose setting and the snap element engages successive dose stops, the torque exerted by the torsion spring increases.

In some instances, it can be desirable to select a biasing member that exerts only enough torque to counter-rotate the snap element to the next lowest dose stop. In such cases, the biasing member will not add any mechanical assistance to the user during the dose delivery procedure. There can also be situations where it is desirable to select and use a biasing member that develops enough torque during dose setting that during dose delivery a mechanical assistance through a counter rotational force is achieved such that a user needs to apply less axial force than would be needed using a biasing member with inherently less torque.

The dose knob is operatively connected to the snap element through a set of splines located on an inner surface of the dose knob. These splines engage and mesh with the fixed set of splines on an outer surface of the snap element during dose setting. The rotation of the dose knob during dose setting causes rotation and axial movement of the snap element and only axial distal movement of the dose selector. The snap element translates axially relative to the housing in the distal direction because the snap element is rotationally fixed to the dose sleeve, which in turn is threadedly connected to an inner surface of the housing. The dose selector does not rotate relative to the housing because it is splined to housing such that it can only move axially relative to the housing. The dose knob is axially fixed to the dose selector, but can rotate relative to the dose selector so that the dose knob, dose selector, dose sleeve and the snap element all move axially relative to the housing during both dose setting and dose delivery.

The snap element has a second set of splines attached to the outer surface of the snap element. This second set of splines or floating spline are a separate component of the dose setting mechanism and are not an integral part of the snap element, i.e., they are not rotationally fixed to the snap element. The floating spline is preferably circumferentially located around an outer surface of the snap element in a free-wheeling fashion such that when the floating spline is rotationally fixed relative to the housing, the snap element will rotate within or relative to the floating spline. The floating spline is configured with a plurality of radial projecting longitudinal splines equally spaced apart from one another. This is in contrast to the dose stops on the inner surface of the dose selector, where the spaces between the dose stops do not have to be equal. However, the space between each of the dose stops is a multiple of the space between each of the radially projecting longitudinal splines of the floating spline component.

To deliver a set dose the user will exert an axial force in a proximal direction relative to the housing on the dose knob. If this axial force is stopped a halted dose delivery situation can arise. The dose setting mechanism of the present disclosure contains a second fail-safe feature to prevent possible problems associated with a halted dose delivery situation. As will be explained in more detail below, the initiation of the dose delivery procedure first involves an axial movement of the dose knob and the dose selector, which is axially fixed to the dose knob. This axial movement of the dose knob also causes disengagement of the splines on the dose knob from the fixed splines on the snap element. This disengagement removes the rotationally fixed relationship between the dose knob and the snap element that exists during the dose setting procedure. The proximal axial movement of dose knob and dose selector that occurs during the initiation of the dose delivery procedure is relative to the housing and, at least initially, relative to the snap element. The axial proximal movement of the dose selector causes the dose stops to move out of radial alignment with the protrusion on the snap element. The dose knob and dose selector is biased in a distal direction relative to the snap element by a second biasing member, which preferably is a compression spring. During dose setting this second biasing member ensures that splines on the dose knob are engaged with the fixed splines on the snap element. However, during dose delivery the distally directed biasing force exerted by the second biasing member is overcome by the user's proximally directed axial force on the dose knob, thus allowing disengagement of the splines.

As stated, during dose delivery, the user exerts a counter axial force in the proximal direction to move the dose knob and dose selector axially relative to the snap element. If the injection is halted and the axial force in the proximal direction is removed or sufficiently decreased, the second biasing member will urge the dose selector back in the distal direction causing the protrusion and the dose stops to come back into alignment and causing the splines on the dose knob to reengage the fixed splines on the snap element. Because the snap element is subject to a counter rotation force from the first biasing member, this will tend to cause both the snap element and the dose knob to rotate in a direction that will reduce the set dose to an unintended, and likely unknown, lower amount. Stated differently, the counter rotation of the snap element will cause the protrusion to rotate to engage the next lower predetermined dose stop. As will be explained in more detail below, the rotation of the snap element also causes rotation of a nut engaged with a piston rod where the position of the nut relative to the piston rod is directly proportional to an amount of medicament to be delivered. Allowing the counter rotation of the snap element in a halted injection situation acts to reduce the intended previously set dose by an amount that can not be determined by the user, thus resulting in a potential dangerous under dosing situation.

The second fail-safe feature of the dose setting mechanism of this disclosure is achieved through the use of a radially projecting circumferential rib that engages a second protrusion on the snap element such that the dose selector can only be pressed and moved in a proximal direction to start a dose delivery when the second protrusion is aligned with a cut-out in the radially projecting rib. This axial proximal movement of the dose selector at the start of the dose delivery moves the radially projecting rib from a first position where the second protrusion is located on the proximal facing side of the rib to a second position. In moving to the second position the rib moves relative to the second protrusion such that the cut-out moves past the second protrusion so that it is then positioned on the distal facing side of the rib. Preferably, the radially projecting rib has a plurality of cut-outs that correspond to each of the dose stops. Once in the second position the rib now can block distal axial movement of dose selector as the snap element begins to counter rotate as dose delivery proceeds if the user releases the proximal directed force on the dose knob. The axial blocking feature occurs because the second biasing member urges the dose selector in the distal direction thus causing an abutment of the second protrusion with the distal facing surface of the rib. This abutment prevents further movement of the dose selector and thus re-engagement of the fixed splines with the splines on the inside of the dose knob.

The second fail-safe feature therefore allows the dose selector to only move in a distal direction during dose delivery when the second protrusion is aligned with a cut-out in the radially projecting rib. If a halted injection occurs when a cut-out in the rib corresponds or aligns with the position of a dose stop, a distal axial movement of the dose selector will occur, but such movement will realign the first protrusion with the corresponding dose stop and will reengage the fixed splines with the dose knob. Since the first protrusion is now re-engaged with a dose stop there can be no counter rotation of the snap element and dose knob relative to housing, and thus no rotation of the nut relative to the piston. The result being there is no reduction in the set dose. Another benefit of this second fail-safe feature is that the dose knob can only move axially relative to the snap element when the protrusion on the snap element is engaged with one of the dose stops of the dose selector. This would prevent an unintended dose delivery if the user were to rotate the dose knob while simultaneously exerting an axial driving force in the proximal direction.

The snap element can also include a clicker arm that engages the radial projecting longitudinal splines on the inner surface of the dose selector during dose delivery such that the rotation of the snap element produces an audible feedback as the clicker arm travels over the radial projecting longitudinal splines. During dose setting, the engagement between the first protrusion on the flexible arm of the snap element and the dose stops generates a first number of tactile and/or audible notifications. During dose delivery, a second number of tactile and/or audible notifications is generated, where the second number of notifications is greater than the first number. In some instances, the second number of notifications is equal to the total number of the splines that correspond to the set predetermined fixed dose. The degree of tactile notification and/or the level of audible notification can be changed by changing the shape and/or the type component materials that are used to fabricate the splines or the clicker arm. Similarly, the dose stops and the first protrusion on the flexible arm can be configured with various shapes or materials of construction to generate distinct tactile and/or audible notifications so that a user will readily discern the difference between dose setting/dose cancelling and dose delivery.

The dose setting mechanism of this disclosure also can contain a clutch that is operatively connected to the dose knob at a distal end of the clutch. In one embodiment, the proximal end of the clutch is rotationally fixed to a nut and is axially slidable relative to the nut. The nut can be threadedly engaged with a piston rod that is configured to move only axially in the proximal direction such that during dose delivery the piston rod exerts an axial force causing a plunger within the container of medicament to move proximally pressurizing the medicament so that it is discharged through a proximal opening in the medicament container. A preferred shape of the piston rod includes one having a non-circular cross-section and having threads on the outside surface. The pitch of these threads is directly proportional to each predetermined fixed dose of medicament. A piston guide having a non-circular center opening can be included in the dose setting mechanism, where the piston guide accepts the non-circular cross-section of the piston rod such that the piston guide prevents the piston rod from rotating during both dose setting and dose delivery.

The dose setting knob and clutch are operatively connected such that they are rotationally fixed to each other so that during dose setting rotation of the dose knob rotates the clutch, which in turn rotates the nut. Rotation of the nut causes the nut to translate axially in a distal direction along threads located on the outer surface of the piston rod during dose setting and to translate in the proximal direction during dose cancellation. During dose delivery, the dose knob is preventing from rotating due to the engagement with the floating spline that is rotationally fixed to the housing. As the clutch is rotationally and axially fixed to the dose knob, the clutch likewise does not rotate and can only move axially in the proximal direction during dose delivery. As such, the nut also does not rotate during dose delivery, moving only axially with the piston rod a distance in a proximal direction. This distance is directly proportional to a set dose. This axial only movement of the nut necessarily causes axial movement of the piston rod because of the threaded engagement with the nut. As mentioned, during dose setting the axial translational movement of the nut in the distal direction is directly proportional to an amount of the medicament that would be delivered if the piston rod was then moved proximally without rotation of the nut relative to the piston rod.

The dose setting knob can also include an anti-rolling feature that prevents the injection device from rolling when a user places the device unattended on a flat surface, such as a table top. To prevent the device from rolling and falling off a surface where the device could be damaged, the dose knob can include a radially projecting rib. This rib prevents the injection device from rolling greater than 180 degrees when the device is placed on a flat surface. The radially projecting rib does not point to, or align with, a corresponding designation on the body of the device. In other words, the relative circumferential position of the rib as the dose knob is turned to set a dose does not correlate with any of the finite set of predetermined fixed doses. To set a dose, the knob is always turned in one direction, for example: clockwise. The knob does not turn during injection. So, with each injection the knob and, as such, the radially projecting rib turns further clockwise. As such, the radial position of the rib cannot correlate with any part of the pen body, in particular not with the predetermined doses.

This disclosure is also directed to complete injection devices. One possible embodiment of such an injection device includes a body with an attachment mechanism at a proximal end configured to connect with a holder for a container, preferably a cartridge, containing a medicament to be delivered to a patient in a series of set doses. A dose setting mechanism as described above can be used in this injection device where the dose selector is configured to allow only a set of finite predetermined fixed doses to be set by a user of the device, where the set of finite predetermined fixed doses includes a lowest fixed dose and one or more higher fixed doses, and wherein at least one of the one or more higher fixed doses is equal to the lowest fixed dose plus a fractional amount of the lowest fixed dose. The dose stops are circumferentially positioned on an inner surface of the dose selector and the circumferential distance between each dose stop and a zero dose hard stop is directly proportional to each fixed dose.

In another embodiment of the injection device of this disclosure the device has a body with an attachment mechanism at a proximal end configured to connect a cartridge holder that holds a cartridge containing a quantity of medicament, where the quantity of medicament is measured in doses. The device further includes a dose setting mechanism having a dose selector rotatably fixed to the body, where the dose selector contains dose stops configured to allow only a finite set of predetermined fixed doses that can be set using the dose setting mechanism. There is also a snap element that is rotatable relative to the dose selector. The snap element has a fixed set of splines integral to an outer surface and arranged circumferentially around the outer surface. The dose setting mechanism further contains a fail-safe component configured to prevent a user of the injection device from setting a dose other than one of the finite set of predetermined fixed unit doses. A floating spline that is axially fixed to the snap element allows the snap element to rotate relative to the floating spline during both dose setting and dose delivery. A dose knob having a first position during dose setting and a second position during dose delivery allows a user to select one of the predetermined fixed doses, where in the first position the dose knob is splined to the fixed set of splines but not splined to the floating spline and when in the second position the dose knob is splined to the floating spline but not the fixed set of splines.

The present disclosure also is directed at methods of designing and manufacturing an injection device based on performing a dose-ranging evaluation. This is possible because of the unique design of the dose setting mechanism where only a single component, namely the dose selector, needs to be replaced with a different dose selector in order that the injection device has a new finite set of predetermined fixed doses or just a single predetermined effective fixed dose. One such method includes providing a first injection device having a first dose setting mechanism that includes a floating spline, a dose knob, a dose selector, and a snap element as described above. The floating spline is engaged with a fixed set of splines on the dose selector during dose setting and dose delivery. Additionally, the floating spline is engaged with splines on the dose knob during dose delivery, but not during dose setting. This first injection device is then used in a dose-ranging evaluation trial where a plurality of the first injection device containing a medicament are distributed to a plurality of trial patients.

The trial patients are instructed to use the first injection devices to perform injections of predetermined doses of the medicament. Physiological data can be collected from the trial patients after the injections are performed in order to analyze the collected physiological data to determine an effective single dose of the medicament. Alternatively, the trial patients can simply report the effects of the injections of the predetermined doses. Based on the analyzed or reported results, a second injection device can be provided that has been manufactured with a second dose setting mechanism where the manufacturing process involves redesigning the dose selector such that the second injection device can be set to a new finite set of predetermined doses or to a single effective fixed dose. The floating spline, the dose knob, and the snap element in the second dose setting mechanism are unchanged in design from that used in the first dose setting mechanism. In other words, only the dose selector must be redesigned and newly manufactured. All other components used to assemble the second dose setting mechanism remain identical to those used in the first dose setting mechanism. In some cases, indicia printing on the outside surface of the dose sleeve can be changed to reflect new predetermined dose setting(s) of the redesigned and newly manufactured dose selector. However, the design, manufacture, and functionality of the dose sleeve remains unchanged.

Another advantage of the dose setting mechanism of the present disclosure that is related to the fact that only a single component needs to be changed to affect a new set of finite predetermined dose settings is that the equipment used for assembly of the complete injection device and the methodology for assembly remains the same. Keeping the same assembly equipment and methodology is directly related to the fact that only the number and location of the dose stops inside the dose selector needs to be changed to arrive at a new injection device.

The above described advantage is directly related to the inherent flexibility of the design of the dose selector to achieve any possible number of predetermined fixed dose settings between a zero dose and a maximum dose, including fractional doses of the lowest set dose. This becomes important for a pharmaceutical company that wants to evaluate a new medicament or to evaluate how an existing medicament will impact a different disease state. Especially beneficial is the ability to easily and efficiently design different dose selectors each having a different finite set of predetermined doses, including having fractional fixed predetermined doses instead of having each fixed dose being a multiple of a lowest fixed dose.

In injection devices of the type disclosed in this disclosure the manufacture of those devices can bring unavoidable tolerances and functional clearances between the single components of the drug delivery device, in particular the components of the dose setting mechanism. As a consequence, clearances such as a gap between those components, such as between the piston rod foot and the sliding piston can occur even after the drug delivery device has been assembled so that the piston may not be in contact with the distal end of the foot. It is, therefore, important to eliminate any such gaps or manufacturing tolerance anomalies so that the dose setting mechanism is in a pre-stressed state prior to the first setting of one of the finite predetermined set doses. If this is not achieved, then it would be possible that the dialed predetermined set dose cannot be accurately dispensed from the device correctly. Initial manufacturing clearances can already falsify the setting of the dose. To adjust the drug delivery device for use, priming actions are conducted to ensure that the drive mechanism is correctly adjusted, e.g. that the piston rod and the attached foot is in contact with the sliding piston so that the correct amount of the medicament can be expelled from the device. These adjustment actions can be achieved in either the manufacturing/assembly procedure of the device or by the user of the assembled device immediately prior to the first use of the device. In the latter scenario the user will need to dispense a small amount of medicament, which gives a visual indication that the drug delivery device is ready to use, but also results in a waste of medicament. The present disclosure describes priming procedures covering both possibilities.

BRIEF DESCRIPTION OF DRAWINGS

The invention will be explained in more detail hereinafter with reference to embodiments of the invention and with reference to the drawings.

DETAILED DESCRIPTION

In the present application, the term "distal part/end" refers to the part/end of the device, or the parts/ends of the components or members thereof, which in accordance with the use of the device, is located the furthest away from a delivery/injection site of a patient. Correspondingly, the term "proximal part/end" refers to the part/end of the device, or the parts/ends of the members thereof, which in accordance with the use of the device is located closest to the delivery/injection site of the patient.

Figure 1:
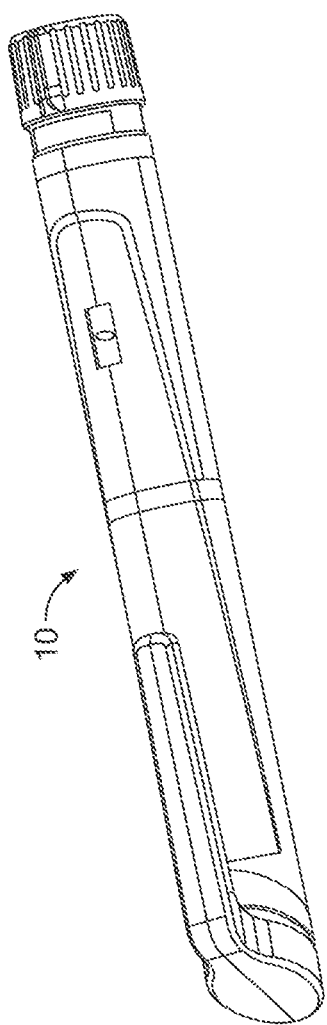
FIG. 1 is a perspective illustration of one possible complete medicament delivery device containing the structural components of the present disclosure.
Figure 2:
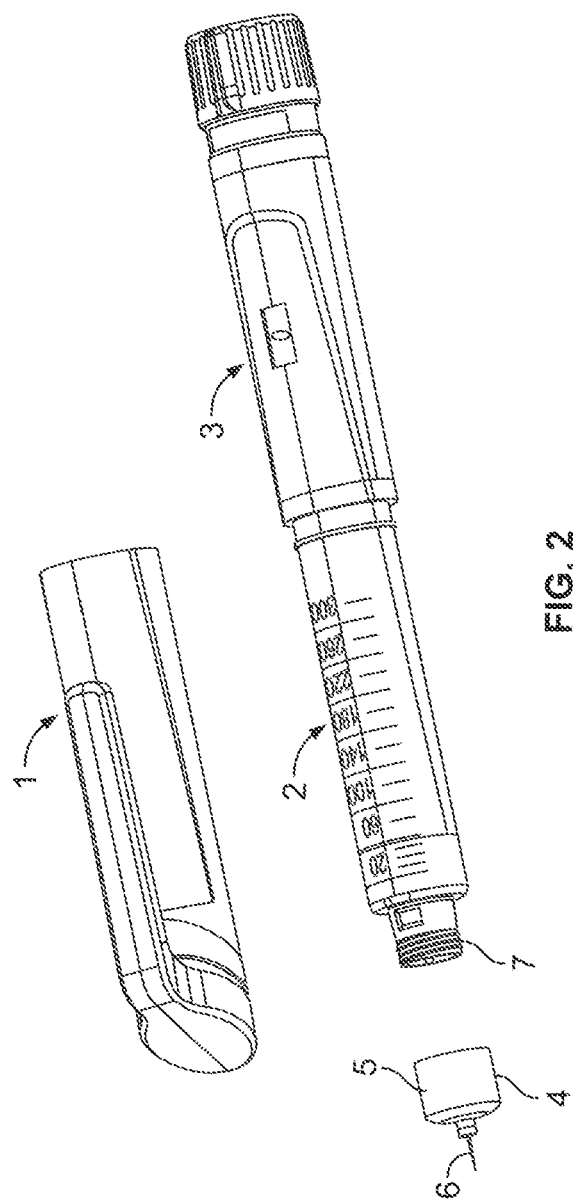
FIG. 2 shows a perspective illustration of the device of FIG. 1 where the cap is removed allowing attachment of a pen needle to the cartridge holder.
Figure 3:
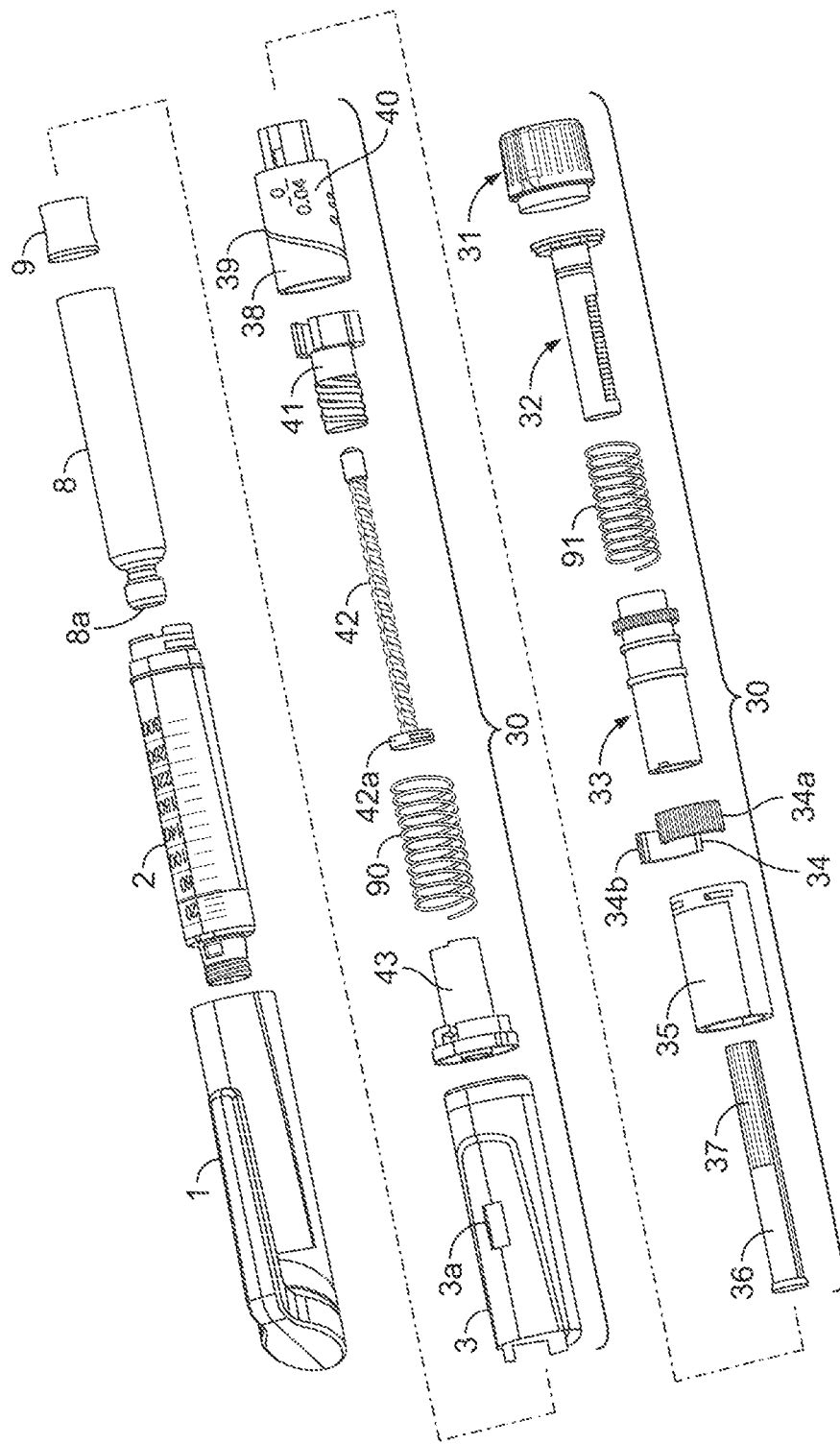
FIG. 3 is an exploded view of the device of FIG. 1.

The dose setting mechanism 30 (see FIG. 3) of the present disclosure can be used in a number of variously designed complete injection devices. One such embodiment of a complete injection device 10 is illustrated in in FIG. 1, which is shown in the zero dose state as indicated by indicia 40 showing a zero through the window 3a of housing 3. FIG. 2 shows the device of FIG. 1 with cap 1 removed to expose the cartridge holder 2 and the proximal needle connector 7. Pen needle 4 is attached to the needle connector 7 through a snap fit, thread, Luer-Lok, or other secure attachment with hub 5 such that a double ended needle cannula 6 can achieve a fluid communication with medicament contained in cartridge 8. The cartridge 8 is sealed at the proximal end by septum 8a and with a sliding piston 9 at the opposite distal end.

As explained above, the dose setting mechanism 30 of the present disclosure is unique compared to other known pen-type injection devices in that only a single component of the dose setting mechanism, namely dose selector 35, is primarily responsible for determining a finite set of predetermined fixed doses within a maximum allowable dose range. Moreover, this finite set of predetermined fixed doses can contain fractional doses, meaning that each fixed dose does not have to be an equal multiple of the other fixed doses. For example, one fixed dose setting can equal an equal multiple of a lower fixed dose plus a fractional amount of that equal multiple.

Figure 6:
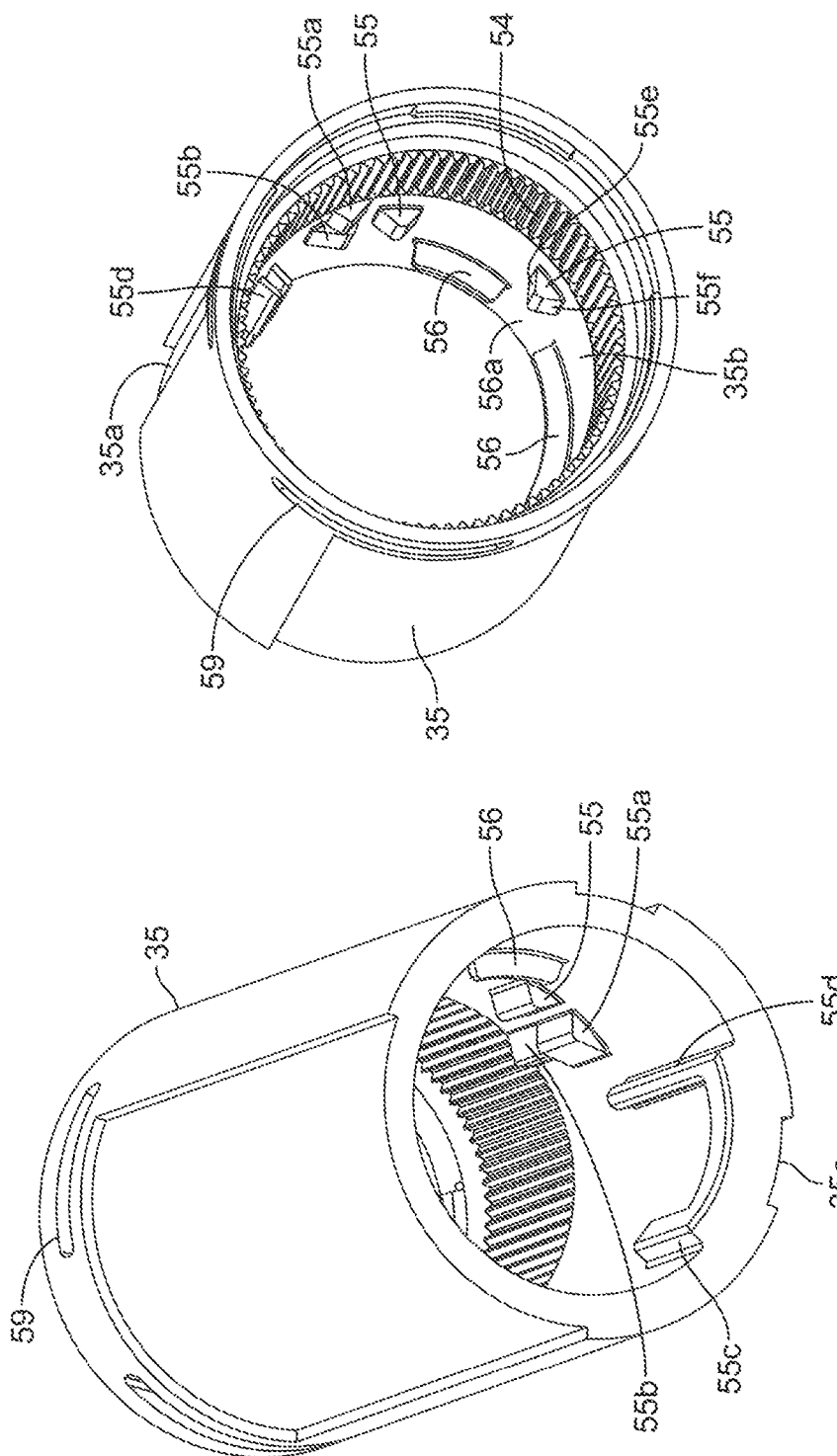
FIG. 6 shows perspective views of the dose selector from both the distal end and the proximal end.
Figure 11:
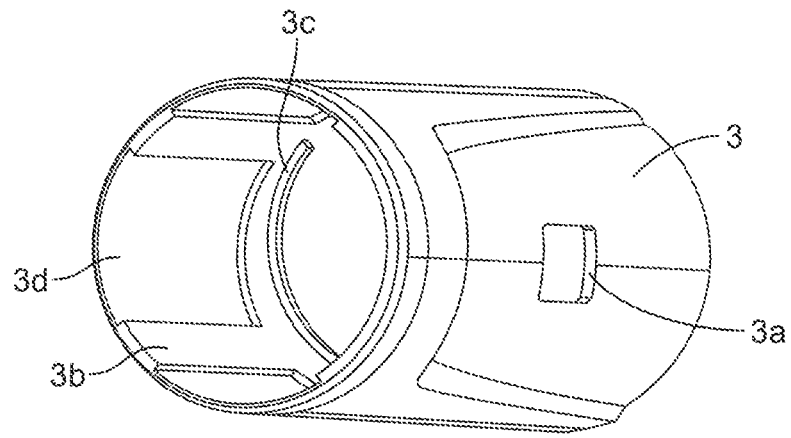
FIG. 11 is a perspective view of the housing of the dose setting mechanism.

The dose selector 35 is shown in FIG. 6 from both a proximal end view and a distal end view. The outer surface of the dose selector has a number of longitudinal grooves 35a that are always engaged with longitudinal splines 3b located on the inner surface 3d of housing 3 (see FIG. 11). This engagement prevents relative rotation between the dose selector and the housing, but allows the dose selector to move axially relative to the housing. The outer surface of the dose selector also has connecting cut-outs 59 that permanently engage and lock with snap fits 31c on the dose knob 31 (see FIG. 12) such that the dose knob is axially fixed to the dose selector 35. These permanent snap fits 31c allow the dose knob to rotate relative to the dose selector during both dose setting and dose cancellation. At the distal end of the inner surface 35b of dose selector 35 there is a set of fixed splines 54. The number and relative spacing between of splines 54 is equal to the number and relative spacing between of fixed splines 31a located on the inside proximal end surface of dose knob 31. The reason for this equivalency, as explained more fully below, is to ensure the smooth transition between the dose setting procedure and the initiation of the dose delivery procedure when the dose knob disengages one set of splines and engages another set of splines. The space between each of the dose stops is a multiple of the space between each of the radially projecting longitudinal splines 52 on floating spline 34.

In one embodiment of the dose setting mechanism of the present disclosure the number of equally spaced splines 52 is chosen to allow for eighty radial positions between knob and snap element. However, for ergonomic and other reasons, the zero dose hard stop 55d and the chosen maximum dose hard stop 55c limit the usable relative rotation of the dose setting knob to 270°. As such, this limited rotation means that there are effectively only 60 (sixty) usable radial positions (80 splines×270°/360°). In one example, a customer can only want an injection device having a maximum dose of 0.60 ml. This would then mean that the sixty radial positions would lead to a raster (or increment) of 0.01 ml. The user could select a fixed dose of 0.20 ml or 0.21 ml for example, but not a dose of 0.205 ml. In most applications, a raster of 0.01 ml is sufficient for any practical use.

In another possible embodiment, if the maximum dose was chosen to be 0.30 ml using the 80 equally spaced splines 52, then this would be a raster of 0.005 ml. This raster is typically finer than needed and an alternative approach for this chosen maximum dose would be to have 40 equally spaced splines instead of 80. The finer the raster the higher is the likelihood that a binding/blocking problem will occur when the splines on the dose knob engage with those on floating spline and the fixed splines 44 of snap element 33. A preferred acceptable radial mismatch should be below 4.5° when 80 splines are used.

As illustrated in FIG. 6, there is a non-contiguous radially projecting circumferential rib 56 also located on the inner surface of dose selector 35 that is selectively interrupted by a number of cut-outs 56a at circumferential locations corresponding to dose stops 55 and to priming stop 55a. The function of this rib 56 and the cut-outs 56a will be explained in more detail below. The dose stops 55 correspond directly to the finite number of predetermined fixed doses that the dose setting mechanism is capable of setting, including in some cases a predetermined fixed priming dose. One or more dose stops can be included on the inner surface of dose selector 35. Preferably, the dose stops 55 are formed as an integral part with the inner surface 35b of dose selector 35 that can be manufactured as a single molded component. A single molded dose selector facilitates an important attribute of the dose setting mechanism of the present disclosure, which is the ability to change a single component of the injection device to obtain a different set of finite predetermined doses. This is achieved by changing the number and/or relative circumferential spacing of the dose stops on the inside of the dose selector.

The inner surface 35b also has a zero dose hard stop 55d. The circumferential spacing between each dose stop 55 and the zero dose hard stop 55d is directly proportional to one of the finite set of predetermined fixed doses. As mentioned, in some cases, it is desirable to include a priming stop 55a corresponding to a fixed priming dose that allows a user to initially position the foot 42a of piston rod 42 in abutment with the distal end surface of piston 9 before a first injection is attempted. This priming step insures that the first injection accurately dispenses a dose of medicament that corresponds to one of the predetermined fixed dose settings. The dose stops 55 and the priming stop 55a are configured with a shape that facilitates dose setting and dose cancelation, as will be explained in more detail below. FIG. 6 shows the dose stops having inclined surfaces 55e and 55f This is in contrast to the zero dose hard stop 55d that is configured as a hard stop.

Also shown in FIG. 6 on the inside surface of the dose selector is an optional end of injection bump 55b. During the dose delivery procedure, as the protrusion 45 rotates with the snap element relative to the dose selector the protrusion will eventually arrive at the end of injection bump 55b when the snap element returns to the zero dose setting. The protrusion will ride up and over the bump 55b generating a notification signal to the user that the injection device 10 has returned to the initial zero dose starting condition. This notification does not necessarily indicate that the expulsion of the set dose medicament is reached, but it does signal to the user to begin the recommended 10 second hold time of needle insertion to ensure complete delivery of the dose.

Figure 4:
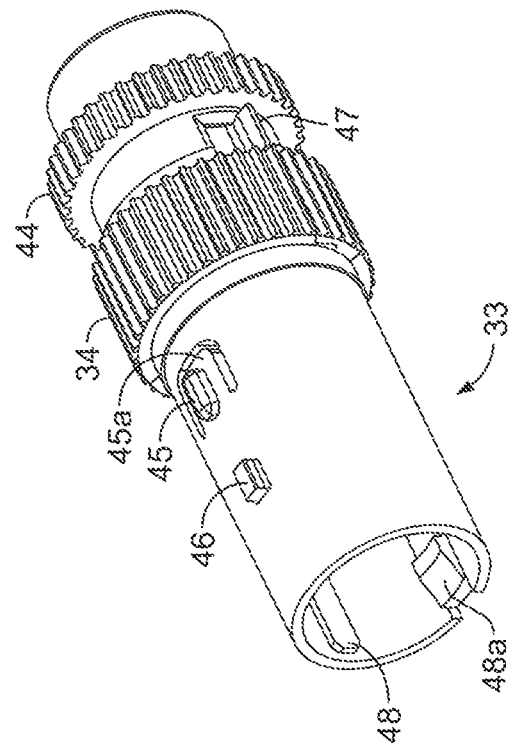
FIG. 4 shows perspective views of the snap element with and without the floating spline rotatably connected thereto.
Figure 4:
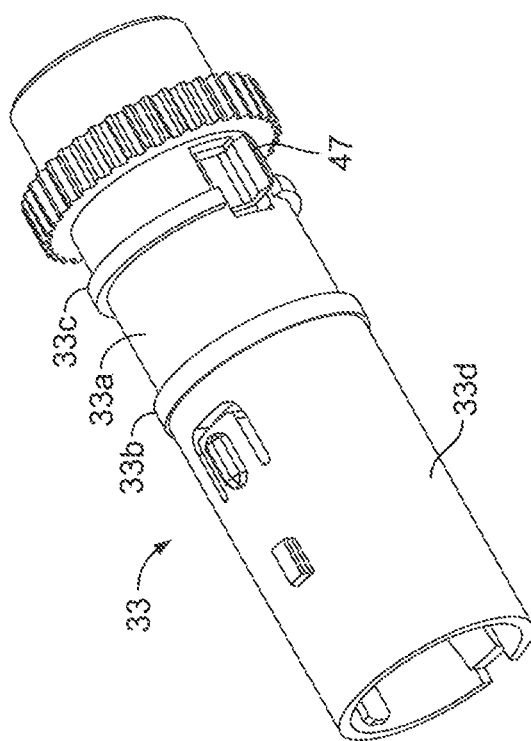

The setting of one or more of the predetermined fixed doses is achieved through the interaction of snap element 33 with dose selector 35. FIG. 4 shows snap element 33 with and without the floating spline 34 rotatably connected to the outer surface 33a of snap element 33. The snap element can be rotationally and axially connected to dose sleeve 38 through splines 48 and snap element 48a. Protrusion 45 is arranged on a flexible arm 45a and only engages the dose stops 55 and priming stop 55a during dose setting and dose cancellation. In other words, for reasons explained below, protrusion 45 does not engage the dose stops during dose delivery as the snap element rotates in a counter-rotation direction relative to the dose selector during dose delivery. A second or blocking protrusion 46 is located on the outer surface 33d at the proximal end of snap element 33. The location of this blocking protrusion is selected so that it can abut the distal facing surface of the radially projecting rib 56 in the event dose delivery is interrupted. As explained below, this abutment will prevent the dose knob from moving axially in the distal direction if during dose delivery the user stops exerting a proximally directed axial force on the dose knob when the dose setting mechanism is in between two predetermined fixed dose settings.

Figure 14A:
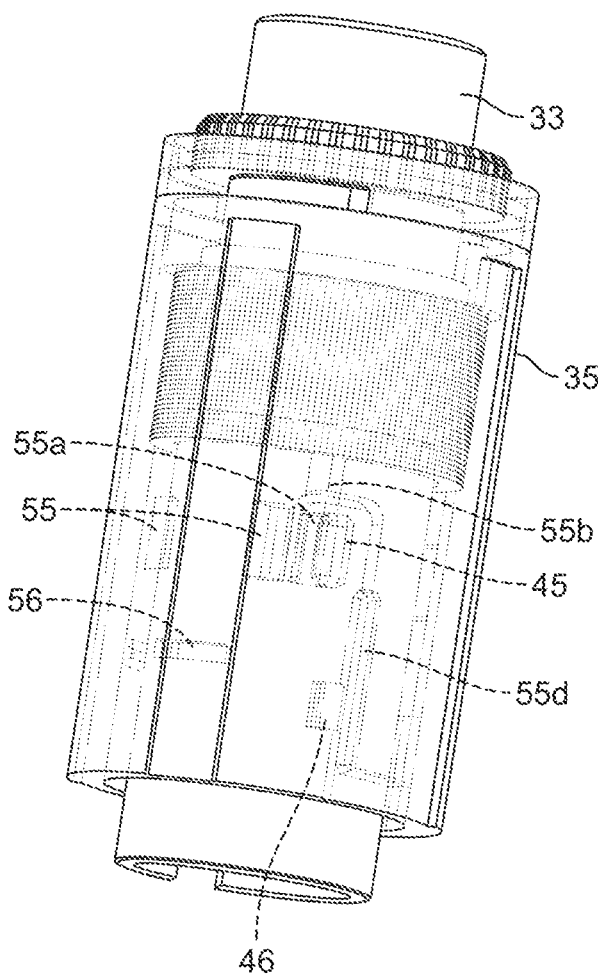
FIGS. 14A-14E illustrate various positions of the snap element relative to the dose selector.
Figure 14B:
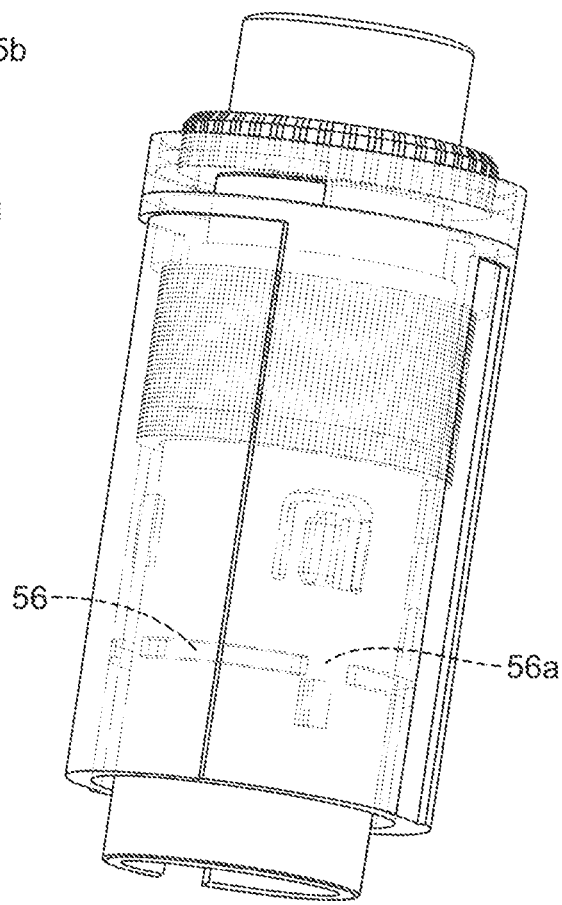

FIGS. 14A-14E illustrate the relative positions of the blocking protrusion 46, the protrusion 45, the projecting rib 56 and the zero dose hard stop 55d and the maximum dose hard stop 55c. FIG. 14A shows the dose setting mechanism in an initial zero set dose position where there is no axial force applied to the dose knob, i.e., a so-called released state. Here blocking protrusion is abutting zero dose hard stop 55d preventing dialing a dose less than zero, i.e., turning the snap element 33 in a clockwise direction. The protrusion 45 is on the back side of priming stop 55a. FIG. 14B shows the dose setting mechanism set with one of the finite predetermined set doses (0.1 ml) set before the dose knob is pressed to initiate the dose delivery procedure. Protrusion 45 is positioned on the front side of dose stop 55 and blocking protrusion 46 is positioned on the proximal side of projecting rib 56, but is in axial alignment with cut-out 56a.

Figure 14C:
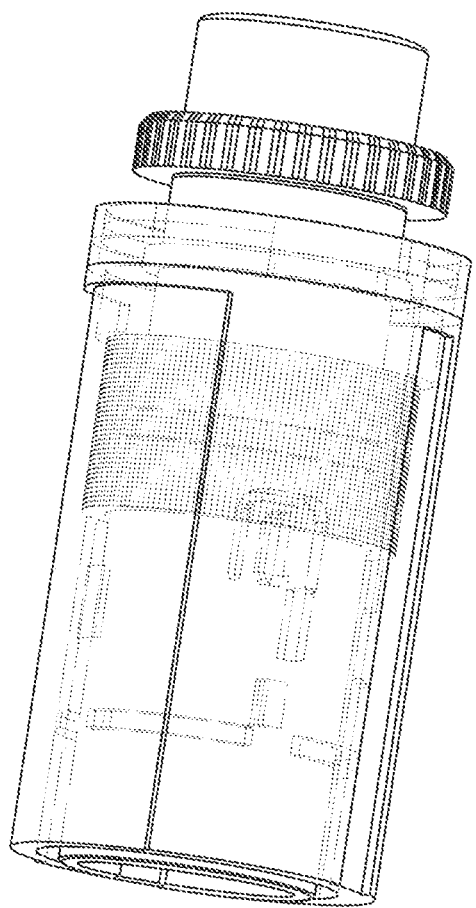

FIG. 14C shows the initiation of the dose delivery of the set 0.10 ml dose of FIG. 14B prior to the beginning of the rotation of the snap element 33. Here the dose selector 35 has now moved proximally relative to the snap element 33 causing the blocking protrusion 46 to be positioned on the distal side of projecting rib 56. This relative position change is only possible because of the cut-out 56a being aligned with the blocking protrusion 46. Dose stops 55 have now come out of radial alignment with protrusion 45, thus allowing snap element 33 to counter-rotate counter clockwise relative to the dose selector as the dose delivery procedure continues.

Figure 14D:
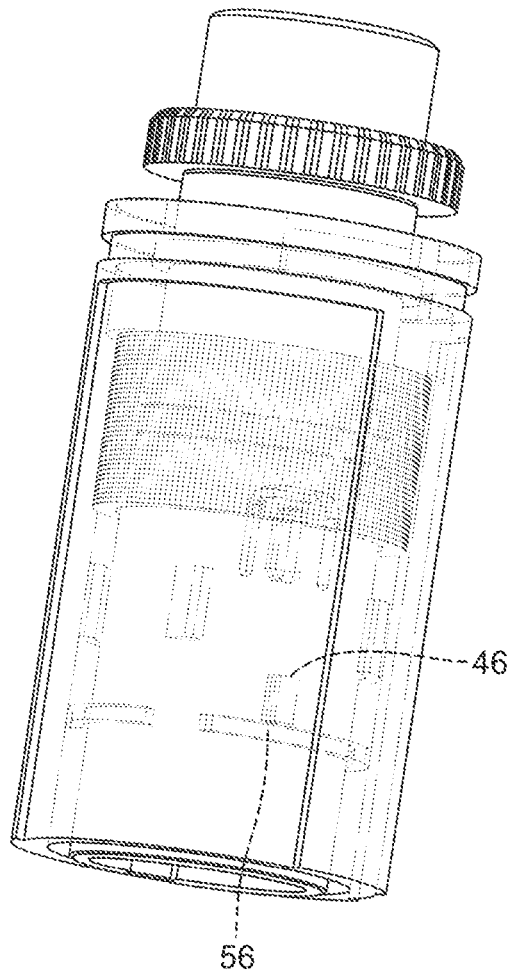
Figure 14E:
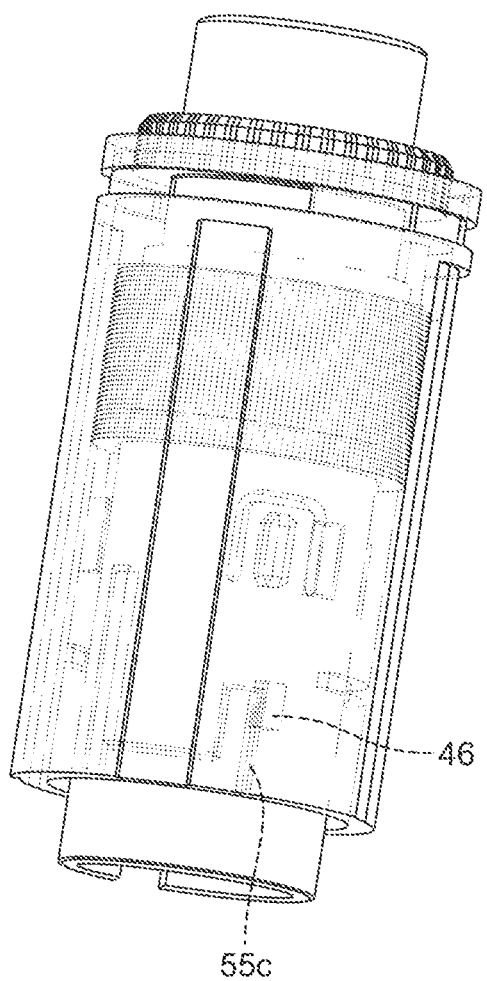

FIG. 14D shows the relative position of the blocking protrusion 46 and the projecting rib 56 in a condition where the user releases (removes) the proximally directed axial force on the dose knob during the dose delivery procedure. The projecting rib 56 comes into abutment with the blocking protrusion 46 thus preventing distal axial movement of the dose selector. This also prevents the splines on the dose knob from reengaging with fixed splines on the snap element. FIG. 14E illustrates the interaction of the maximum dose hard stop 55c with the blocking protrusion 46 in cases where the user dials past the maximum predetermined fixed dose setting. As illustrated the protrusion 45 has moved up and over the maximum predetermined fixed dose stop 55 and the blocking protrusion is in abutment with the maximum dose hard stop 55c preventing any further rotation of the snap element 33.

Snap element 33 also has a set of fixed splines 44, preferably that are formed integral to the snap element during the manufacture of the snap element, for example during a molding process. These fixed splines 44 do not rotate or move axially relative to the snap element. The number and spacing of these splines 44 are equal to that of splines 54 on the inner surface of the dose selector and the splines 31a on the inside of the dose knob. The function of splines 44 will be explained below. Snap element 33 also can have a clicker 47, shown in FIG. 4 as a flexible arm with a radially directed nib. The clicker is configured to engage the splines 31a on the dose knob only during dose delivery such that rotation of the snap element produces an audible and/or tactile feedback as the clicker nib travels over the splines 31a of dose knob 31. During dose setting the engagement of protrusion 45 with dose stops 55 and priming stop 55a also produces tactile and/or audible notification, but only as each predetermined dose setting is reached. The number of notifications during dose setting is less than the number of notifications generated by the clicker 47 during dose delivery. This is because the clicker engages each of the equally spaced splines on the inside surface of the dose knob.

Figure 5:
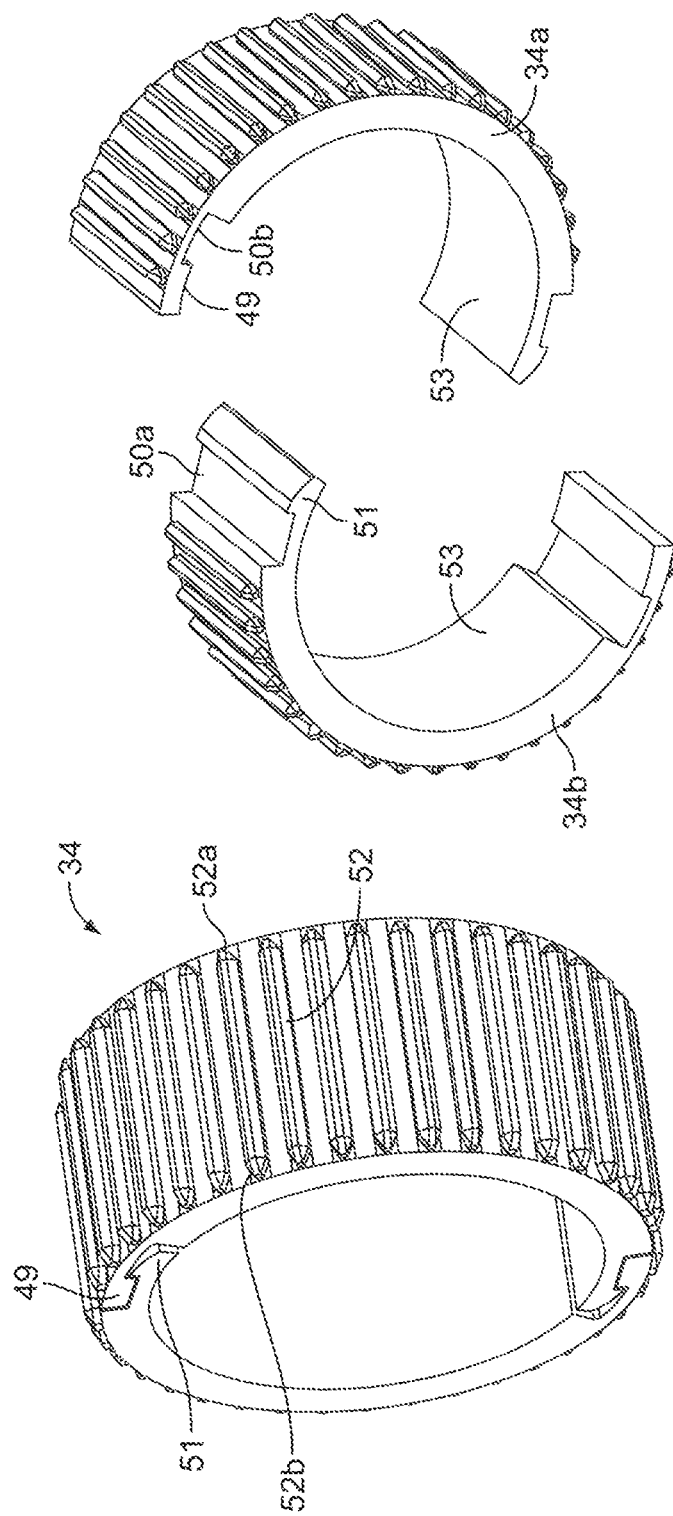
FIG. 5 shows perspective views of the floating spline in both an assembled state and in a pre-assembled state.

The snap element 33 also has an outer surface 33a that accepts and axially contains floating spline 34. The floating spline is axially contained to limit the axial movement of the floating spline relative to the snap element. As indicated in FIG. 4, the axial containment of the floating spline to prevent movement distally and proximally is achieved by radial ribs 33b, 33c that define outer surface 33a. Floating spline 34 is shown in FIG. 5, where a preferred configuration is two halves 34a, 34b that can be connected to each other after assembly onto surface 33a. The connection of the two halves can be through a snap fit shown as the combination of arms 49, 51 engaging detents 50a, 50b, respectively. Regardless of the connection type, it is important that the engagement with the snap element 33 is such that the floating spline and snap element can rotate relative to each other. The number and spacing of the splines 52 on the floating spline 34 are equal to that of splines 44, equal to splines 54 on the inner surface of the dose selector, and the splines 31a on the inner surface of the dose knob. This is necessary because the floating spline 34 functions as a connector, as explained in more detail below, during dose delivery where the dose knob is prevented from rotating relative to the dose selector 35. When the dose setting mechanism is assembled, the splines 54 on the inner surface of dose selector 35 are fully engaged or meshed with splines 52. This meshing of splines 52 and 54 rotationally fixes the floating spline 34 to the dose selector 35. Since the dose selector 35 is splined to the housing 3 to prevent rotation, this results in the floating spline 34 also being rotationally fixed to housing 3.

As shown in FIG. 5, the terminal proximal end 52a and terminal distal end 52b of each spline 52 is chamfered to assist in the smooth meshing with splines 31a on dose knob 31 during the initiation of dose delivery. When the dose setting mechanism is assembled, the dose knob 31 is splined to the snap element 33 through meshing of only splines 44 and splines 31a on the dose knob. Because splines 44 are fixed rotationally to snap 24 element 33, rotation of dose knob 31 necessarily causes rotation of snap element 33 such that surface 33a rotates relative to the rotationally fixed inner surface 53 of floating spline 34. This rotation of the dose knob and snap element occurs during dose setting and is relative to housing 3. During the initiation of the dose delivery procedure the dose knob is pressed in the proximal direction causing it to move axially relative to the snap element. This initial movement disengages splines 31a from splines 44 and causes splines 31a to then engage floating spline 34. This new engagement of splines 31a and 34 then prevents the dose knob from rotating relative to the housing 3 during dose delivery.

Figure 12:
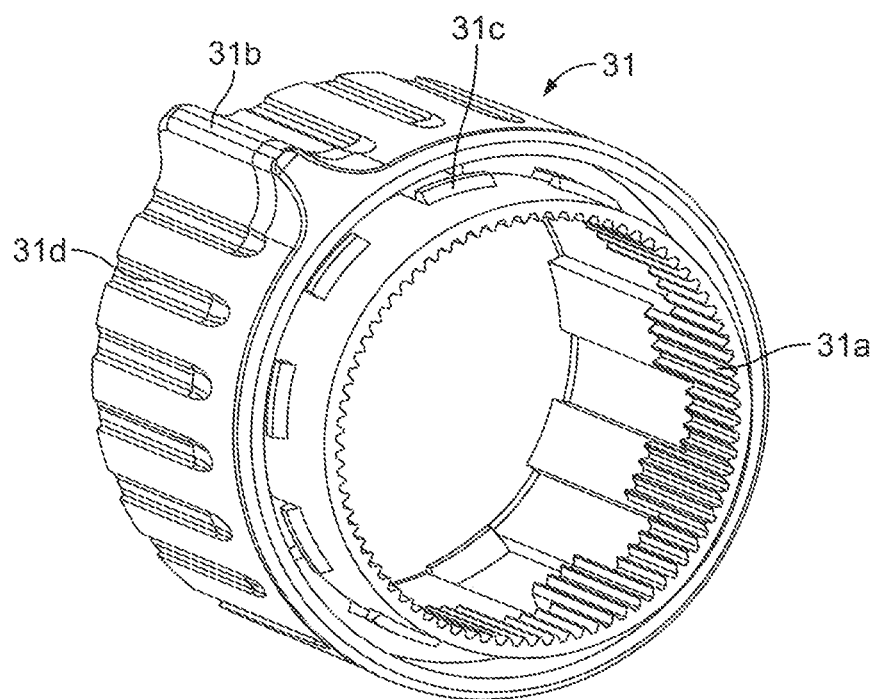
FIG. 12 is a perspective view of the dose knob.

Details of dose knob 31 are illustrated in FIG. 12. During assembly of dose setting mechanism the dose knob is axially fixed and attached to dose selector 35 through snap elements 31c that are engaged with corresponding cut-outs 59. This connection allows the dose knob to rotate relative to the dose selector. The dose knob also has gripping surfaces 31d on the outer surface and includes a radially projecting rib 31b that functions as an anti-roll feature, as well as, a leverage feature to assist the user in setting or cancelling a dose.

Figure 9:
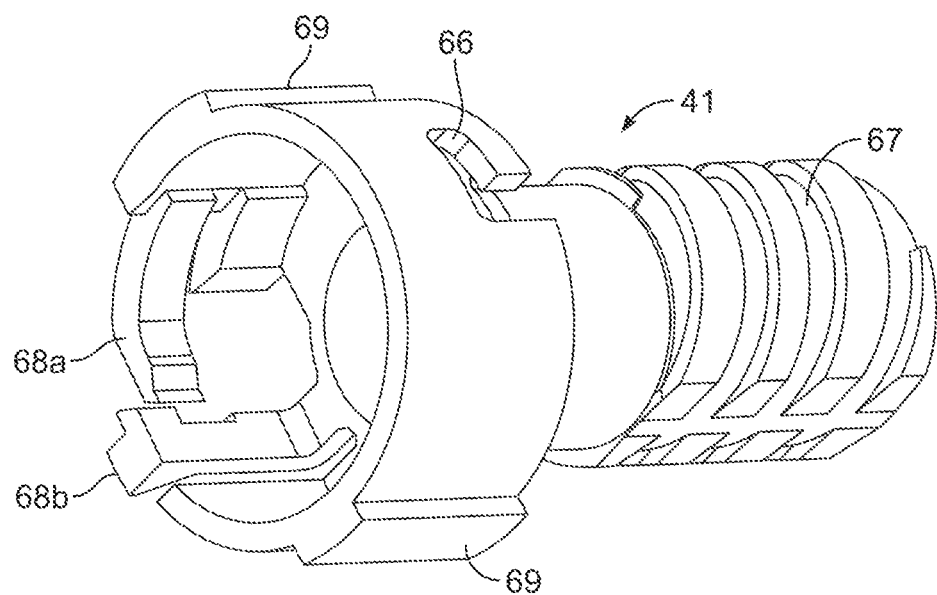
FIG. 9 is a perspective view of the driver.
Figure 10:
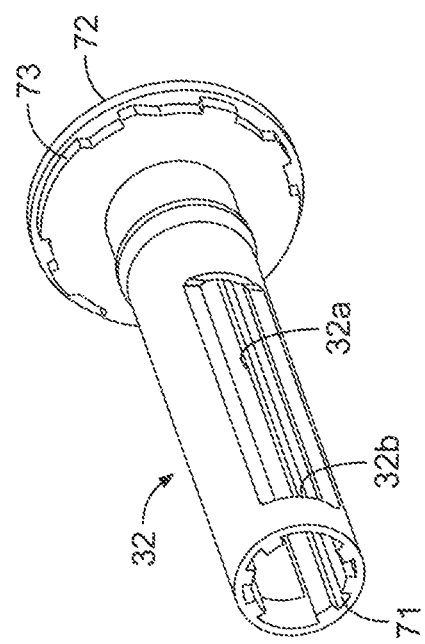
FIG. 10 is a perspective exploded view of the nut and the clutch.
Figure 10:
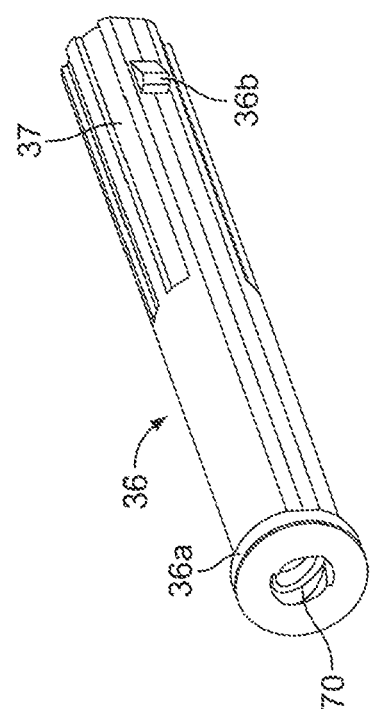

FIG. 10 illustrates the nut 36 and the clutch 32 which are permanently splined to each other during assembly of the dose setting mechanism through a splined connection. The splined connection is established by connection elements 37 of nut 36 and connection elements 71 of clutch 32. This splined connection ensures that clutch 32 and nut 36 are always rotationally fixed to each other during both dose setting and dose delivery. This splined connection also allows the clutch and the nut to move axially relative to each other. The sliding connection is necessary in order to compensate for pitch differences between the threads 60 on the piston rod 42 (see FIG. 8), the outer thread 39 on the dose sleeve 38 (see FIG. 3) and the thread 67 on the driver 41 (see FIG. 9). The sliding connection is necessary to compensate for the difference in the pitch of the thread between nut and the outer surface of the piston rod and the pitch of the thread between dose sleeve and body. The thread between driver and piston guide has basically the same pitch as the thread between piston rod and nut.

The proximal end of nut 36 has internal threads 70 that match threads 60 of piston rod 42. The distal end of clutch 32 is configured as a dose button 72 and is permanently attached to distal end of the dose knob 31 through engagement of connectors 32e and 73, which can also include snap locks, an adhesive and/or a sonic weld. This connection ensures that the clutch is both rotationally and axially fixed to the dose knob during both dose setting and dose delivery.

Figure 8:
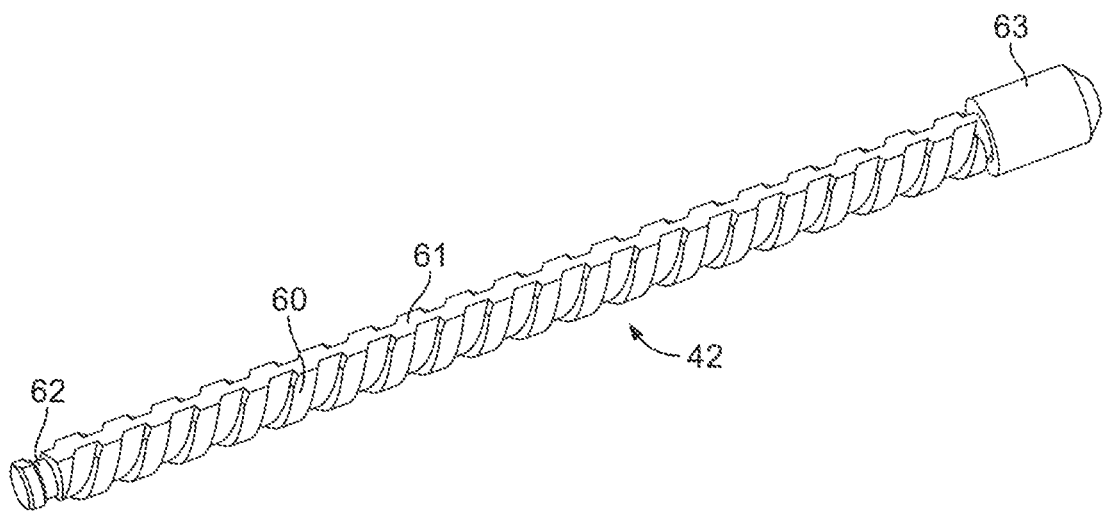
FIG. 8 is a perspective view of the piston rod.

As shown in FIG. 8, in addition to threads 60 on the outer surface of the piston rod 42, there is also included two longitudinal flats 61 that give piston rod 42 a non-circular cross section. At the terminal proximal end is connector 62, shown as a snap fit, that connects with a disc or foot 42a (see FIG. 3). At the distal end of piston rod 42 is a last dose feature of the dose setting mechanism, illustrated as an enlarged section 63. This enlarged section 63 is designed to stop the rotation of nut 36 about threads 60 when the amount of medicament remaining in the cartridge 8 is less than the next highest predetermined dose setting. In other words, if the user tries to set one of the predetermined fixed dose settings that exceeds the amount of medicament remaining in the cartridge, then the enlarged section 63 will act as a hard stop preventing the nut from further rotation along threads 60 as the user attempts to reach the desired predetermined fixed dose setting.

Figure 7:
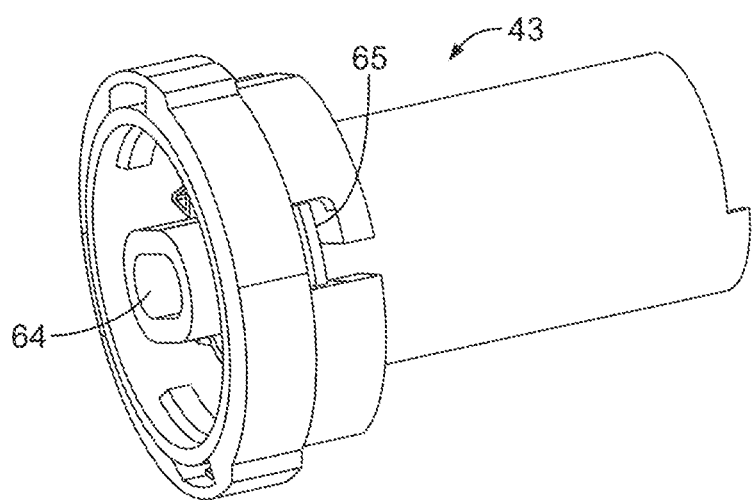
FIG. 7 is a perspective view of the piston guide.

The piston rod 42 is held in a non-rotational state relative to housing 3 during both dose setting and dose delivery because it is arranged within the non-circular pass through hole 64 in the center of piston rod guide 43 (see FIG. 7). The piston rod guide is both rotationally and axially fixed to housing 3. This fixation can be achieved when the piston rod guide is a separate component from the housing 3 as illustrated in the figures or the piston rod guide could be made integral with the housing. Piston rod guide 43 also has a connector 65 configured to engage the proximal end of a rotational biasing member, shown in FIG. 3 as torsion spring 90, the function of which will be explained below. This connection of the rotational biasing member to the piston rod guide anchors one end in a rotational fixed position relative to the housing.

The distal end of the rotational biasing member, for example torsion spring 90, is connected to connector 66 on the driver 41 (see FIG. 9). Driver 41 is connected and rotationally fixed with the inner surface of dose sleeve 38 through splines 69 on the distal outer surface of the driver. On the proximal end of driver 41 on the outer surface are threads 67 that are engaged with matching threads on the inner distal surface of the piston rod guide 43. The thread between driver and piston guide has a significantly different pitch than the thread between dose sleeve and housing. The nut and the driver rotate together both during dose setting and dose cancellation and, as such, they perform essentially the same axial movement. However, this movement is independent from each other, i.e., the nut is turned by the clutch and performs an axial movement due to the thread to the piston rod, while the driver is rotated by the dose sleeve and performs an axial movement due to the thread to the piston guide. The driver is rotating during injection also, and so it actively moves in the proximal direction during injection. But, the nut does not rotate during injection and as such does not perform an active axial movement. The nut is only moving in proximal direction during injection because it is being pushed axially by the driver. The rotating driver pushing the non-rotating nut causes the injection because the piston rod is pushed forward due to the threaded engagement with the nut.

If, for example, the thread of the nut had a higher pitch than the thread of the driver, the nut could not freely move in the distal direction during dose setting because it would be hindered by the slower moving driver. As such, this would cause the drug to be expelled during dose setting. Alternatively, if the thread of the nut had a significantly lower pitch than the thread of the driver, the driver would move away from the nut during dose setting and the driver would not push the nut at the beginning of the injection already, but would do so only after the gap is closed. Accordingly, it is preferred that the pitch of the thread on the driver is equal or slightly higher than the pitch of the thread on the nut. And, the thread between the dose sleeve and the housing has a higher pitch than that of the nut and piston rod. This is desirable because it yields a mechanical advantage that makes the dose delivery process easier for the user. For example, when pushing the knob a distance of 15 mm, the piston rod only moves by 4.1 mm. This results in a gearing ratio of about 3.6:1. A lower gearing ratio would result in an increase of the force the user needs to complete the injection.

As will be explained in more detail below, because the torsion spring is attached to the driver 41 and the driver is rotationally fixed to the dose sleeve 38, then rotation of the dose sleeve in a first direction during dose setting will wind the torsion spring such that it exerts a counter rotational force on the dose sleeve in an opposite second direction. This counter rotational force biases the dose sleeve to rotate in a dose canceling direction and provides the necessary force for the first fail-safe feature mentioned earlier.

The function of the complete injection device 10 and the dose setting mechanism 30 according to this disclosure will now be described. Injection device 10 is provided to a user with or without the cartridge 8 of medicament positioned within the cartridge holder 2. If the injection device 10 is configured as a reusable device, then cartridge holder 2 is connected to housing 3 of the dose setting mechanism 30 in a releasable and reusable manner. This allows the user to replace the cartridge with a new full cartridge when all the medicament is expelled or injected from the cartridge. If the device is configured as a disposable injection device, then the cartridge of medicament is not replaceable because the connection between the cartridge holder 2 and the housing 3 is permanent. Only through breaking or deformation of this connection can the cartridge be removed from the injection device. Such a disposable device is designed to be thrown out once the medicament has been expelled from the cartridge.

The user first removes the cap 1 from the device and installs an appropriate pen needle 4 to the cartridge holder 2 using connector 7. If the device is not pre-primed during the device assembly, or does not have an automatic or forced priming feature as discussed above, then the user will need to manually prime the device as follows. The dose knob 31 is rotated such that the protrusion 45 engages a first dose stop, such as the priming stop 55a, which corresponds to a predetermined small fixed dose of medicament. Rotation of the dose knob rotates protrusion 45 on snap element 33 relative to dose selector 35 because the fixed splines 44 are meshed with splines 31a on the dose knob. During dose setting an axial biasing member, shown in FIG. 3 as a compression spring 91, which is located between the snap element and dose knob, exerts an axial force on the dose knob in the distal direction to ensure that splines 44 and 31a are and remain engaged during dose setting.

Figure 13:
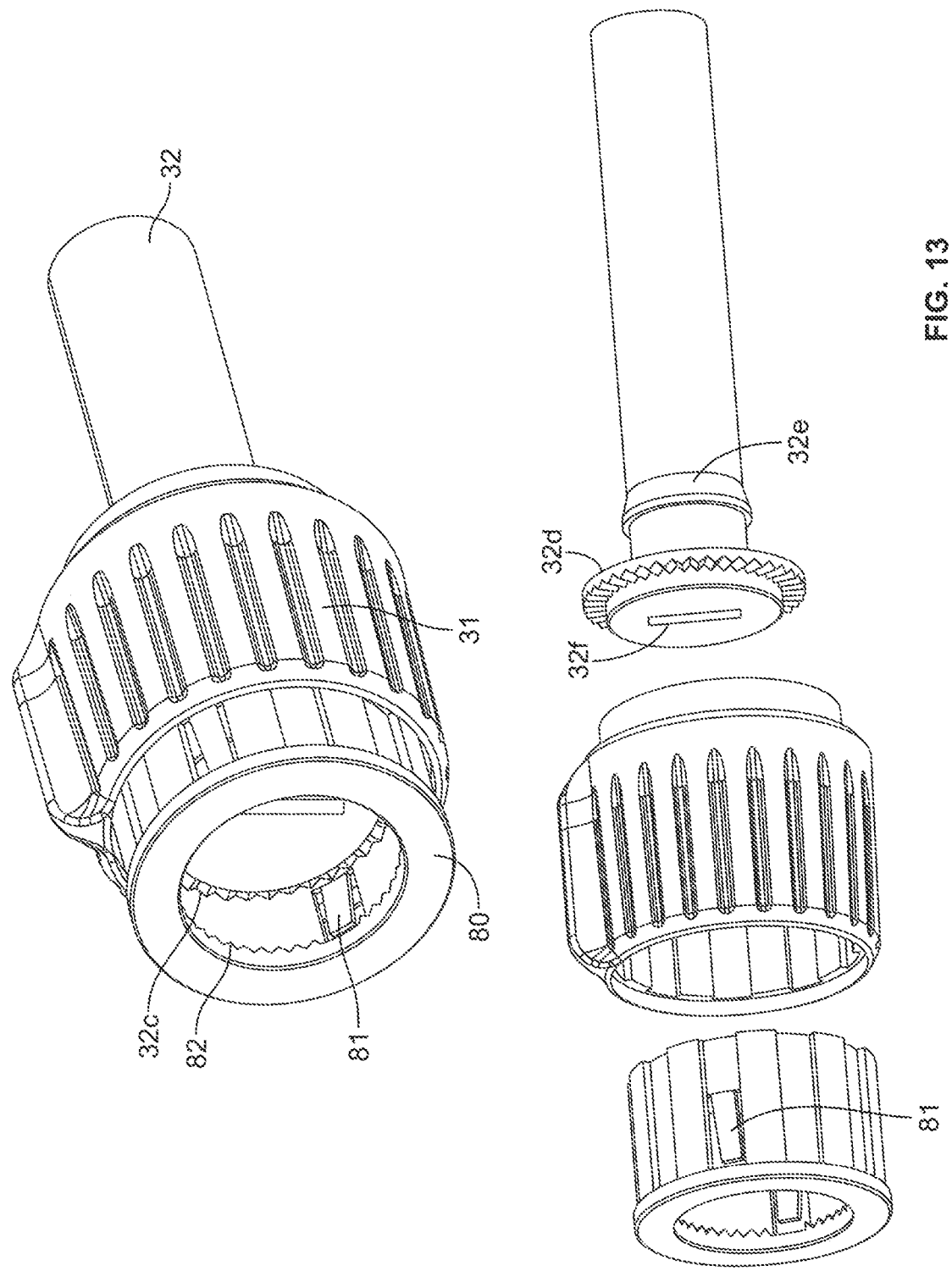
FIG. 13 illustrates a possible forced priming feature of the dose setting mechanism.

The injection device 10 of this disclosure can also have a so-called forced or automatic priming feature, one embodiment of which is illustrated in FIG. 13, where the clutch 32 is initially not rotatably fixed to the dose knob 31. A sliding lock 80 is located between the distal end of the clutch and the inside surface of the dose knob. Prior to using the dose setting mechanism, i.e., before a user could dial one of the predetermined fixed dose settings, the sliding lock 80 would necessarily need to be pushed in the proximal direction such that it moves distally relative to the dose knob. This axial movement causes the snap fingers 81 to engage the proximally facing surface 32d of the clutch, forming an irreversible locking relationship between the dose knob and the distal end of the clutch. This locking relationship also causes teeth 32c of clutch 32 and the corresponding teeth 82 of sliding lock 80 to mesh and interlock such that the dose knob and clutch are rotationally fixed to each other. Before the sliding lock 80 is engaged with the clutch, the clutch can be rotated, which also causes rotation of the nut, to cause the piston rod 42 to move axially relative to the housing. The clutch is rotated until a visual observation and/or tactile notification indicates that the foot 42a located on the piston rod 42 is in firm abutment with the distal facing surface of the sliding piston 9. This abutment between the foot and the sliding piston will ensure that an accurate dialed dose will be delivered out of the needle cannula. This rotation of the clutch is preferably performed during the assembly of the injection device and likewise after ensuring abutment of the foot with the sliding piston 9; the manufacturing process would cause the sliding lock 80 to be pushed to the final, locked position. One possible means to achieve rotation of the clutch would be to use a gripper with a vacuum cup to turn the clutch. Alternatively, a slot or other connector could be designed into the distal surface of the clutch that cooperates with a matching tool in order to engage and rotate the clutch. This optional connector is shown as a slit 32f in FIG. 13.

The rotation of protrusion 45 and subsequent contact with one side of the priming stop 55a, or for that matter any of the predetermined dose stops on the dose selector, will cause the flexible arm 45a to flex radially inward allowing the protrusion 45 to ride up, over and down the reverse side of the dose stops 55a, 55. This movement and contact of the protrusion 45 generates the audible and/or tactile notification that a dose stop has been reached during the dose setting procedure. The type or level of notification can be modified by changing the design of protrusion 45, flexible arm 45a, and/or configuration of the dose stops 55 or priming stop 55a. In some cases, it can be desirable to have different notifications for each of the predetermined dose settings. Likewise, it can also be desirable to have the notifications during dose setting be different than the notifications generated by clicker 47 during dose delivery.

Returning to the priming procedure, once the priming stop 55a is reached, the user can need to cancel the priming procedure and can do so by using the dose canceling procedure. This cancellation procedure also applies to any of the predetermined dose settings. Dose cancellation is accomplished by turning the dose knob in the opposite direction so that the protrusion 45 is caused to counter rotate in the opposite direction relative to the dose stop 55 or priming stop 55a. This will again generate a notification that can be the same or different as the dose setting notification and/or dose delivery notification. Because the snap element 33 is rotationally fixed to the dose sleeve 38, and the dose sleeve is threaded engaged to the inner surface of housing 3, rotation of the dose knob during dose setting and dose cancellation causes relative rotation between the dose sleeve and the housing. The threaded connection between the housing and the dose sleeve causes the dose sleeve, snap element, clutch, and dose knob to translate axially as the dose knob is rotated. During dose cancellation, these components rotate and translate axially in the opposite or proximal direction.

Rotation of the dose knob also causes rotation of nut 36 about threads 60 on the outer surface of piston rod 42, which does not rotate and remains axially fixed relative to the housing 3 because of relative pitch differences in the threaded parts as explained above. The rotation of the nut relative to the stationary piston rod, which is supported by its contact with the sliding piston, causes the nut to translate or climb up the piston rod in the distal direction. A reverse rotation during dose cancellation causes the nut to translate in the reverse direction relative to piston rod. The distance traveled by the nut to achieve the desired dose setting is directly proportional to an amount of medicament that would be expelled if the dose delivery procedure were initiated and completed. Because the pitch of the threaded connection between the dose sleeve and the housing is greater than pitch of the threads on the nut, the dose sleeve, snap element, clutch and dose knob will travel a greater axial distance than the nut as it climbs up or down the piston rod. The difference in axial movement would normally bind the dose setting mechanism, but does not do so because the difference in pitch is compensated for by the sliding splined connection between the nut and the clutch, thus allowing the clutch to travel axially a greater distance longitudinally than the nut. During injection, the clutch pushes on the snap element and as such on the dose sleeve. This axial force causes the dose sleeve to turn due to the thread to the body. The dose sleeve will only start to turn when it is pushed, if the pitch of the thread is high enough. If the pitch is too low the pushing will not cause rotation because the low pitch thread becomes what is called a "self-locking thread."

Rotation of the dose knob also causes rotation of the driver because of the splined rotationally fixed connection to the dose sleeve. Since the torsion spring 90 is fixed at one end to the driver and at the other end to the piston rod guide, which in turn is fixed axially and rotationally to the housing, the torsion spring is wound up increasing in tension during dose setting. As mentioned, the torque of the tension spring exerts a counter rotational force on the dose sleeve. Preferably during assembly of the dose setting mechanism, the torsion spring is pre-tensioned so that even at the zero dose condition the torsion spring exerts a counter rotational force on the dose sleeve. The counter rotation force provides a first fail-safe feature of the dose setting mechanism. This first fail-safe mechanism prevents a user from setting a dose that is not one of the finite set of predetermined dose settings. In other words, if a user is rotating the dose knob and the protrusion 45 is between two dose stops, or between the zero dose hard stop and a first dose stop 55 or a priming stop 55a, and the user releases the dose knob, the counter rotational force of the torsion spring will return the protrusion to the last engaged dose stop or to the zero dose hard stop. Additionally, during a dose cancellation procedure the counter rotational force will assist the user in rotating the dose knob back down to the next lower fixed dose setting or possibly all the way back to the zero dose setting.

During dose setting, the dose knob translates out and away from the distal end of housing 3. As the dose sleeve rotates and translates, the progress of the dose setting (or dose cancellation) is observed in window 3a of housing 3 as the printed indicia 40 on the dose sleeve moves past the open window. When a desired predetermined dose setting is reached the indicia for that dose will appear in the window. Because the dose stop 55 or the priming stop 55a is engaged with the protrusion 45, the torsion spring will not have sufficient force to counter rotate the set dose to the next lower fixed dose setting. At this point the injection device 10 is ready for a priming procedure or, if already primed, the delivery of the medicament to an injection site. In either case, the user will push on the dose knob in the proximal direction until the zero dose hard stop 55d is reached and a zero dose indicia is observed in the window. During a priming step the user will observe whether medicament is expelled out of the cannula 6 of pen needle 4. If no medicament is expelled this means the piston foot 42a is not in abutment with the distal surface of sliding piston 9. The priming step is then repeated until medicament is observed exiting the cannula.

The dose setting mechanism of the present disclosure can also have a maximum dose hard stop feature that prevents a user from setting a dose greater than the highest predetermined dose setting. This is achieved through the use of a maximum dose hard stop 55c that comes into engagement with second protrusion 46 if a user dials, i.e. rotates the dose knob, past the dose stop corresponding to the highest predetermined dose setting. (see FIGS. 4 and 6). The engagement of the second protrusion with the maximum dose hard stop 55c will prevent further rotation of the snap element. The maximum dose hard stop 55c is configured with a shape such that the second protrusion 46 cannot be rotated past the hard stop without deforming or breaking one or more components of the dose setting mechanism. In the event a user dials past the last dose stop and engages the maximum dose hard stop 55c with the second protrusion 46, a release of the dose knob will allow the torsion spring to counter rotate the dose sleeve, snap element and dose knob back to the last dose stop.

The dose setting mechanism also can have an anti-counterfeit or anti-disassembly feature that corresponds generally to the maximum dose hard stop. This anti-counterfeit feature is formed between a hard stop or hook 36b located on the outside surface of nut 36 and a distal facing end wall 32b of a cut-out 32a of clutch 32 (see FIG. 10). As mentioned, the difference in pitch between threads 60 of the piston rod 42 and the outer threads 39 of the dose sleeve 38 requires that the clutch translates further distally than the nut 36 as it climbs up the piston rod 42 during dose setting. The cut-out 32a and/or hard stop 36b can be positioned so that the axial translation of the clutch relative to the piston rod is stopped at a predetermined position that generally corresponds to the engagement of the second protrusion with the maximum dose hard stop. The interaction of the hard stop 36b with the distally facing wall 32b will prevent further distal movement of the clutch relative to the nut and thus can prevent disassembly of the dose setting mechanism. Typically, an attempt to disassemble the injection device is for the purposes of replacing the expelled cartridge of medicament with a counterfeit cartridge to allow the injection device to be sold and reused as a faux new device. The anti-counterfeit feature inhibits disassembly if a person were to pull on the dose knob, which pulls on the clutch, and which in turn pulls on the snap element 33 and dose sleeve 38. Although the threaded connection of the dose sleeve with the inside of the housing works as a primary disassembly feature, when the device is dialed to the maximum dose setting, this primary disassembly feature can not be sufficient to prevent disassembly. The secondary disassembly feature where the hard stop 36b engages facing wall 32b as described above can compensate for this insufficiency.

Once the dose setting mechanism is primed, the user then selects and sets a desired fixed dose by repeating the same steps used for priming except that the dose knob will be rotated past the priming stop 55a until the appropriate dose stop is engaged by the protrusion 45 and the desired dose value appears in the window 3a. In some cases, it is preferred to have no indicia show in the window when dialing between predetermined dose settings, while in other cases it is desirable to show an indicia in the window that is indicative of a non-settable dose position between the fixed dose settings.

Once one of the predetermined dose settings has been dialed on the dose setting mechanism, the user can then exert an axial force in the proximal direction to initiate the dose delivery procedure. The axial force exerted by the user overcomes the distally directed force exerted by the second biasing member 91 causing the dose knob 31, clutch 32 and dose selector 35 to move axially in the proximal direction relative to the snap element 33 and housing 3. This initial movement disengages the splines 31a from splines 44 and causes engagement of splines 31a with floating spline 34, thus rotationally fixing the clutch and dose knob to the housing through the splined connection between the floating spline 34 and splines 54. Splines 54 and floating spline 34 remain engaged during dose setting and during dose delivery even though the dose selector 35 moves axially with the dose knob 31 and relative to the floating spline 34.

The initial axial movement of the dose selector relative to the snap element causes the dose stops to come out of radial alignment with protrusion 45 such that a rotation of the snap element relative to the dose selector would not allow the protrusion 45 to engage any of the dose stops, except of course the end of injection bump 55b, which provides an audible and/or tactile notification, i.e., a so-called end of injection notification, to the user that the mechanical dose delivery procedure of the device is completed. As mentioned, this notification also informs the user to maintain the cannula in the injection site for the recommended time, typically 10 seconds. Likewise, the initial axial movement of the dose selector relative to the snap element also moves the radially projecting rib 56 proximally relative to the second protrusion 46 such that the protrusion 46 faces the distal side of the projecting rib 56 when rotation of the snap element relative to the dose selector occurs during the remaining dose delivery procedure. The projecting rib is able to move axially past second protrusion 46 because of the cut-outs 56a that are in the projecting rib 56 in positions coinciding with each dose stop 55a, 55. At the end of injection, further rotation of the snap element will cause the second protrusion to abut zero dose hard stop 55d, which will prevent any further rotation of the snap element.

In addition to the end of injection feature described above, another end of injection notification feature can be incorporated as part of driver 41. This alternative or additional end of injection feature also provides tactile and/or audible notification to the user when the mechanical dose delivery procedure is complete. One configuration of this end of injection feature is shown in FIG. 9 as the combination of flexible arms 68a, 68b. The flexible arm 68b is loaded during dose setting by a geometry of the inside of the dose sleeve 38. This holds arm 68b inside of the dose sleeve 38 because the flexible arm 68b is bent to the right and inwards (see FIG. 9) and held in place by the flexible arm 68a. When reaching zero after dose delivery, the flexible arm 68a is bent by a geometry of the dose sleeve to release flexible arm 68b. This is possible because the driver 41 is turned by the dose sleeve 38, so that both components have a purely linear movement relative to each other due to the difference in the pitch of the two respective threads 39 and 67.

As the user maintains the axial force on both the dose knob 31 and the dose button 72 during the continuation of the dose delivery procedure, the clutch 32 will abut the distal end of the snap element causing it to move axially in the proximal direction. The clutch pushes on the snap element. The snap element is fixed to the dose sleeve, so the clutch pushes on the dose sleeve. As the dose sleeve has a thread with a sufficiently high pitch relative to the body, the axial force on the dose sleeve will cause the dose sleeve and as such the snap element to turn relative to the body, and by turning relative to the body it moves in the proximal direction. The dose selector slides into the housing, but does not rotate relative to the housing 3 due to the splined engagement between spline 3b and the groove 35a. The rotation of the dose sleeve 38 also causes rotation of the driver 41 into the threaded connection with piston rod guide 43, which drives the piston rod proximally and results in a concurrent de-tensioning of torsion spring 90. The driver does not directly drive the piston rod. As the driver rotates, the driver moves in the proximal direction and pushes the nut forwards. As the nut doesn't turn, the driver pushes the nut and the piston rod forward.

The nut 36 does not rotate during dose delivery because of the rotationally fixed relationship with clutch 32 that is rotationally fixed to the housing through rotationally fixed relationship of the dose knob, floating spline and the housing. The nut therefore can only move axially carrying the piston rod 42 with it because the piston rod is prevented from rotating by the non-circular opening 64 engaged with the flats 61 on the piston rod. The piston rod is moved axially the same distance that the nut originally translated relative to the piston rod during dose setting. This axial movement without rotation is caused by the rotational and axial movement of the proximal end of the driver in abutment with flange 36a of the nut. Axial movement of the piston rod causes the sliding piston 9 to also move axially relative to the inside walls of the stationary cartridge 8 forcing an amount of medicament out of the needle cannula 6 that is equivalent to the predetermined fixed dose that was set during the dose setting procedure.

If the user stops the dose delivery procedure by removing the axial force on the dose knob the second fail-safe mechanism is activated. Removal of the axial force causes the compression spring 91 to bias the dose knob in the distal direction. If the user halts the dose delivery between two predetermined fixed dose settings, then the dose knob and the axially fixed dose selector will both be prevented from moving proximally because the second protrusion 46 will come into abutment with the distally facing side of projecting rib 56, which will stop the axial movement of dose selector and dose knob. Without this abutment of protrusion 46 with projecting rib 56, the dose selector would move distally such that the splines 31a would re-engage with splines 44 on the snap element, thus placing the dose knob, clutch and nut back into rotational engagement with the snap element. The torque exerted on the snap element through the driver would then counter rotate the nut, thus reducing the set dose by an unknown amount. This counter rotation would continue until the next lowest predetermined fixed dose setting is reached, where the corresponding dose stop would stop the counter rotation.

If on the other hand the dose delivery is halted at one of the lower predetermined fixed dose settings, the cut-out 56a in the projecting rib 56 would allow dose selector to move distally such that the second protrusion 46 is positioned on the proximal side of rib 56. This would also re-engage the splines 31a of dose knob 31 with the fixed splines 44 placing the dose knob, clutch and nut into rotational engagement with the snap element as described above. However, because the cut-outs 56a are only located at circumferential positions corresponding to the dose stops, there will be no counter-rotation of the snap element, and hence the nut, because the dose stop and the first protrusion 45 are engaged. Because there is no counter rotation of the nut, there can be no unknown reduction in the set dose. Therefore, a resumption of the halted dose delivery procedure will continue without any unknown decrease in the set dose, thus allowing the originally set predetermined dose to be delivered.

It is to be understood that the embodiments described above and shown in the drawings are to be regarded only as non-limiting examples of the possible designs of the safety assembly and such designs can be modified in many ways within the scope of the patent claims.

What is claimed:

1. A dose setting mechanism for an injection device, the dose setting mechanism comprising:
   a dose knob;
   a dose selector comprising at least one dose stop that corresponds to one of a finite set of one or more predetermined fixed dose settings; and
   a snap element,
   the snap element being configured to interact with the dose selector to set the one or more predetermined fixed dose settings,
   the snap element being configured to rotate relative to the dose selector during dose delivery, and
   the snap element being configured such that, at an end of the dose delivery, further rotation of the snap element causes a protrusion of the snap element to abut a zero dose hard stop of the dose selector to prevent any further rotation of the snap element,
   the zero dose hard stop being different from the at least one dose stop.

2. The dose setting mechanism of claim 1, wherein the protrusion is configured to abut the zero dose hard stop to prevent dialing of a dose less than zero when the dose setting mechanism is in an initial zero set dose position.

3. The dose setting mechanism of claim 1, wherein the zero dose hard stop is located on an inner surface of the dose selector.

4. The dose setting mechanism of claim 1, wherein the dose knob is configured to be pushed in a proximal direction during dose delivery until the protrusion reaches the zero dose hard stop.

5. The dose setting mechanism of claim 1, wherein one or more dose stops are located on an inner surface of the dose selector, and engagement of a second protrusion of the snap element with one of the one or more dose stops sets a single fixed dose of medicament for delivery.

6. The dose setting mechanism of claim 1, wherein rotation of the dose knob during dose setting causes rotation and axial movement of the snap element and only axial movement of the dose selector.

7. The dose setting mechanism of claim 1, wherein:
the dose knob is configured to be rotated during dose setting to set the finite set of the one or more predetermined fixed dose settings, and
the dose knob includes a radially projecting rib.

8. A dose setting mechanism for an injection device comprising:
a dose knob;
a dose selector comprising at least one dose stop that corresponds to one of a finite set of one or more predetermlined fixed dose settings; and
a snap element,
the snap element being configured to interact with the dose selector to set the one or more predetermined fixed dose settings,
the snap element being configured to rotate relative to the dose selector during dose setting, the dose setting mechanism comprising a maximum dose hard stop that is engaged if a user dials past a maximum predetermined dose setting,
the maximum dose hard stop being disposed on the dose selector, and
a protrusion of the snap element being configured to interact with the maximum dose hard stop if the user dials past the maximum predetermined dose setting.

9. The dose setting mechanism of claim 8, wherein engagement of the protrusion with the maximum dose hard stop will prevent further rotation of the snap element.

10. The dose setting mechanism of claim 8, wherein the maximum dose hard stop has a shape such that the protrusion cannot be rotated past the maximum dose hard stop without deforming or breaking one or more components of the dose setting mechanism.

11. The dose setting mechanism of claim 8, wherein one or more dose stops are located on an inner surface of the dose selector, and engagement of a second protrusion of the snap element with one of the one or more dose stops sets a single fixed dose of medicament for delivery.

12. The dose setting mechanism of claim 8, wherein the finite set of one or more predetermined fixed dose settings is defined only by a number of and relative spacing between the at least one dose stop such that replacing the dose selector with a second dose selector having a different arrangement of dose stops results in the dose setting mechanism having a different set of finite predetermined fixed dose settings.

13. A dose setting mechanism comprising:
a dose knob;
a dose selector comprising at least one dose stop that corresponds to one of a finite set of one or more predetermined fixed dose settings; and
a snap element,
the snap element being configured to interact with the dose selector to set the one or more predetermined fixed dose settings,
the snap element being configured to rotate relative to the dose selector during dose setting, the dose knob being axially fixed to the dose selector, and
the dose knob being configured to rotate relative to the dose selector during both dose setting and dose cancellation.

14. The dose setting mechanism of claim 13, wherein the dose knob comprises snap elements that are configured to be engaged with corresponding cut-outs of the dose selector.

15. The dose setting mechanism of claim 13, wherein an interaction between a protrusion on the snap element and a circumferential rib on the dose selector prevents proximal movement of the dose knob unless a dose has been set.

16. The dose setting mechanism of claim 13, wherein an initiation of a dose delivery procedure includes an axial movement of the dose knob and the dose selector, which is axially fixed to the dose knob.

17. The dose setting mechanism of claim 13, wherein the dose knob and the dose selector are biased in a distal direction relative to the snap element by a biasing member.

18. The dose setting mechanism of claim 13, wherein delivery of a set dose requires an axial driving force applied in a proximal direction to the dose knob.

19. The dose setting mechanism of claim 18, wherein:
the dose knob and the dose selector are configured to move axially in the proximal direction relative to the snap element at an initiation of a dose delivery procedure,
the dose selector comprises a radially projecting circumferential rib that engages a protrusion on the snap element such that the dose selector can only be pressed and moved in the proximal direction to start the dose delivery procedure when the protrusion is aligned with a cut-out in the radially projecting rib.

* * * * *